United States Patent [19]

Wächtler et al.

[11] Patent Number: 4,751,017
[45] Date of Patent: Jun. 14, 1988

[54] HETEROCYCLIC BORON COMPOUNDS

[75] Inventors: Andreas Wächtler, Griesheim; Joachim Krause, Dieburg; Rudolf Eidenschink, Münster; Jürgen Eichler, Breuberg; Bernhard Scheuble, Alsbach, all of Fed. Rep. of Germany

[73] Assignee: Merck Patent Gesellschaft mit beschrankter Haftung, Darmstadt, Fed. Rep. of Germany

[21] Appl. No.: 843,404

[22] Filed: Mar. 24, 1986

[30] Foreign Application Priority Data

Mar. 22, 1985 [DE] Fed. Rep. of Germany ....... 3510424

[51] Int. Cl.$^4$ .......................... G02F 1/13; C09K 19/34
[52] U.S. Cl. .................... 252/299.61; 252/299.5; 350/350 R; 350/350 S; 544/229; 546/13; 549/370; 558/286; 558/288; 558/289; 558/290; 558/298
[58] Field of Search .......................... 250/350 R, 350 S; 252/299.5, 299.61

[56] References Cited

U.S. PATENT DOCUMENTS

| | | | |
|---|---|---|---|
| 3,038,926 | 6/1962 | Farthouat | 252/299.61 |
| 3,997,536 | 12/1976 | Boller et al. | 252/299.61 |
| 4,062,798 | 12/1977 | Boller et al. | 252/299.61 |
| 4,200,580 | 4/1980 | Hsu | 252/299.61 |
| 4,311,610 | 1/1982 | Zaschke et al. | 252/299.61 |
| 4,313,878 | 2/1982 | Hsu | 252/299.61 |
| 4,322,354 | 3/1982 | Sorkin | 252/299.61 |
| 4,323,504 | 4/1982 | Sethofer | 252/299.61 |
| 4,325,830 | 4/1982 | Sethofer | 252/299.61 |
| 4,348,324 | 9/1982 | Demus et al. | 252/299.61 |
| 4,356,104 | 10/1982 | Hsu | 252/299.61 |
| 4,358,393 | 11/1982 | Zaschke et al. | 252/299.61 |
| 4,389,329 | 6/1983 | Boller et al. | 252/299.61 |
| 4,486,332 | 12/1984 | Demus et al. | 252/299.61 |
| 4,510,069 | 4/1985 | Eidenschine et al. | 252/299.63 |
| 4,512,636 | 4/1985 | Andrews et al. | 252/299.61 |
| 4,521,327 | 6/1985 | Demus et al. | 252/299.61 |
| 4,533,488 | 8/1985 | Fukui et al. | 252/299.61 |
| 4,565,425 | 1/1986 | Petrzilka et al. | 252/299.61 |
| 4,581,155 | 4/1986 | Goto et al. | 252/299.61 |
| 4,615,824 | 10/1986 | Demus et al. | 252/299.5 |
| 4,623,477 | 11/1986 | Ogawa et al. | 252/299.61 |
| 4,632,515 | 12/1986 | Gray et al. | 252/299.61 |

FOREIGN PATENT DOCUMENTS

| | | | |
|---|---|---|---|
| 56501 | 7/1982 | European Pat. Off. | 252/299.61 |
| 84194 | 7/1983 | European Pat. Off. | 252/299.61 |
| 2257588 | 6/1973 | Fed. Rep. of Germany | 252/299.61 |
| 3405914 | 8/1985 | Fed. Rep. of Germany | 252/299.61 |
| 3404116 | 8/1985 | Fed. Rep. of Germany | 252/299.61 |
| 158480 | 1/1980 | German Democratic Rep. | 252/299.61 |
| 58-136680 | 8/1983 | Japan | 252/299.61 |
| 61-83190 | 4/1986 | Japan | 252/299.61 |
| 61-97293 | 5/1986 | Japan | 252/299.61 |
| 61-109792 | 5/1986 | Japan | 252/299.61 |
| 2092169 | 8/1982 | United Kingdom | 252/299.61 |

OTHER PUBLICATIONS

Seto, K. et al., J. Chem. Soc., Chem. Commun., pp. 122–123 (Feb. 1975).
Seto, K. et al., Mol. Cryst. Liq. Cryst., Lett. Sect., vol. 2, No. 6, pp. 197–200 (1985).
C. A., vol. 105, 70537r (1986).

*Primary Examiner*—Teddy S. Gron
*Attorney, Agent, or Firm*—Millen & White

[57] ABSTRACT

Heterocyclic boron compounds of the formula I

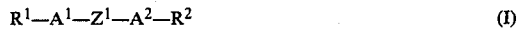

can be used as components of liquid-crystal phases. $A^1$ is —A—, —$A^4$—A—, or —A—$A^4$— and A is

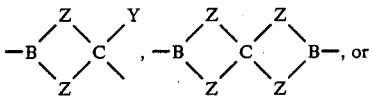

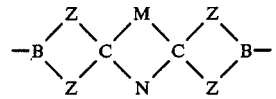

15 Claims, No Drawings

HETEROCYCLIC BORON COMPOUNDS

BACKGROUND OF THE INVENTION

This invention relates to liquid crystalline heterocyclic boron compounds.

Substituted 2-phenyl-1,3,2-dioxaborinanes are disclosed, for example, in U.S. Pat. No. 3,038,926 and are described as suitable for use in medicaments. Seto et al., *J. Chem. Soc.*, Chem. Commun. 1985 122, describe 2,5-diphenyl-1,3,2-dioxaborinanes which have liquid-crystal properties. However, the majority of the compounds disclosed therein have relatively high melting points and narrow meso-phase ranges, which make them less suitable as components of liquid-crystal phases.

SUMMARY OF THE INVENTION

It is an object of this invention to provide new, stable, liquid-crystal or mesogenic compounds suitable for use as components of liquid-crystal phases.

Upon further study of the specification and appended claims, further objects and advantages of this invention will become apparent to those skilled in the art.

These objects have been achieved by providing the use of heterocyclic boron compounds of the formula I

$$R^1-A^1-Z^1-A^2-R^2 \quad (I)$$

wherein $R^1$ and $R^2$ are independently alkyl having 1-15C atoms wherein one or two non-adjacent $CH_2$ groups can also be replaced by —O—, —CO—, —O—CO—, —CO—O— and/or —CH=CH—, one of the radicals $R^1$ and $R^2$ can also be H, F, Cl, Br, NCS, CN or $R^3-A^3-Z^2$—, $A^1$ is —A—, —$A^4$—A— or —A—$A^4$—, A is

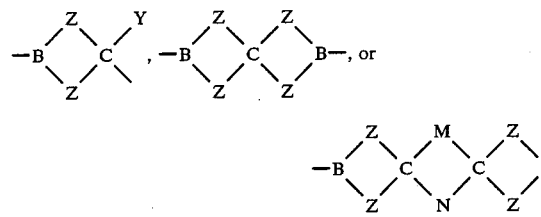

wherein the Zs are identical or different and are —N=CH—, —NH—$CH_2$—, —O—$CH_2$— or —S—$CH_2$— which are not linked to boron via a carbon atom, M and N are each independently —$CH_2$—, —CO—, —$CH_2CH_2$—, —$CH_2$—O— or —O—$CH_2$—, and Y is H or $C_1$-$C_4$-alkyl wherein one $CH_2$ group can also be replaced by —O— —CO—, —OCO— Or —COO—, or is F, Cl, Br, $CF_3$— CN, $A^2$, $A^3$ and $A^4$ are each a 1,4-cyclohexylene group wherein one or two non-adjacent $CH_2$ groups can also be replaced by —O— and/or —S—, and/or which can be substituted in the 1-position by $C_1$-$C_4$-alkyl, F, Cl, Br, $CF_3$ or CN, or are a piperidine-1,4-diyl or 1,4-bicyclo[2,2,2]octylene group, A or a 1,4-phenylene group which is unsubstituted or substituted by one or two F and/or Cl atoms and/or $CH_3$ groups and/or CN groups and/or in which one or more CH groups can also be replaced by N, $Z^1$ and $Z^2$ are each independently —CO—O—, —O—CO—, —$CH_2CH_2$—, —CHCN—$CH_2$—, —$CH_2$—CHCN—, —CH=CH—, —O$CH_2$—, —$CH_2$—O—, —CH=N—, —N=CH—, —NO=N—, —N=NO— or a single bond and $R^3$ is alkyl having 1-15C atoms wherein one or two non-adjacent $CH_2$ groups can be replaced by —O—, —CO—, —O—CO—, —CO—O— and/or —CH=CH—, or is H, F, Cl, Br, NCS or CN, subject to the proviso that, if A is 1,3,2-dioxaborinane-2,5-diyl, the latter is not simultaneously substituted by phenyl in the 2-position and the 5-position, and the acid addition salts of the basic members among these compounds as components of liquid-crystal phases.

For the sake of simplicity, in the following text Cy is a 1,4-cyclohexylene group, OBO is a 1,3,2-dioxaborinane-2,5-diyl group, OBS is a 1,3,2-oxathiaborinane-2,5-diyl group, OBN is a 2,5-dihydro-6H-1,3,2-oxazaborine-2,5-diyl group, OBNH is a 1,3,2-oxazaborinane-2,5-diyl group, SBS is a 1,3,2-dithiaborinane-2,5-diyl group, SBN is a 2,5-dihydro-6H-1,3,2-thiazaborine-2,5-diyl group, SBNH is a 1,3,2-thiazaborinane-2,5-diyl group, NBN is a 2,5-dihydro-6H-1,3,2-diazaborine-2,5-diyl group, NBNH is a 2,3,4,5-tetrahydro-6H-1,3,2-diazaborine-2,5-diyl group, NHBNH is a 1,3,2-diazaborinane-2,5-diyl group, Dio is a 1,3-dioxane-2,5-diyl group, Dit is a 1,3-dithiane-2,5-diyl group, Bi is a bicyclo[2,2,2]octylene group, Pip is a piperidine-1,4-diyl group, Phe is a 1,4-phenylene group, Pyr is a pyrimidine-2,5-diyl group and Pyn is a pyridazine-3,6-diyl group, it being possible for Pyr and/or Pyn to be unsubstituted or substituted by one or two F and/or Cl atoms and/or for Pyn to be unsubstituted or substituted by one or two F and/or Cl atoms and/or $CH_3$ groups and/or CN groups.

The compounds of the formula I can be used as components of liquid-crystal phases, in particular for displays which are based on the principle of the twisted cell, the guest-host effect, the effect of the deformation of aligned phases or the effect of dynamic scattering.

Despite the prior art, it has now been found, surprisingly, that the compounds of the formula I are excellently suitable for use as components of liquid-crystal phases. In particular, it is possible to prepare by means of them stable, liquid-crystal phases having a broad meso-phase range and a relatively low viscosity. Furthermore, the compounds of the formula I are distinguished by particularly advantageous elastic constants.

In addition, the range of liquid-crystal substances which are suitable from various aspects of technical performance in use for the preparation of liquid-crystal mixtures is considerably broadened, in a very general way, by the provision of the compounds of the formula I.

The compounds of the formula I possess a wide field of use. Depending on the selection of substituents, these compounds can be used as the base materials of which liquid-crystal phases are predominantly composed; it is also possible, however, to add compounds of the formula I to liquid-crystal base materials belonging to other classes of compounds, in order, for example, to affect the dielectric and/or optical anisotropy of a dielectric of this type. The compounds of the formula I are also suitable for use as intermediate products for the preparation of other substances which can be used as constituents of liquid-crystal dielectrics.

In the pure state the compounds of the formula I are colorless, and they form liquid-crystal meso-phases within a temperature range which is advantageously situated for electrooptical use. They are very stable to chemicals, heat and light.

The invention relates, therefore, to the use of compounds of the formula I. The invention also relates to compounds of the formula I which has the meaning indicated above, but in which $R^1$ and $R^2$ independently are alkyl having 2-15C atoms wherein one or two non-adjacent $CH_2$ groups can also be replaced by —O—, —CO—, —O—CO—, —CO—O— and/or —CH=CH—, one of the radicals $R^1$ and $R^2$ is also F, Cl, Br, NCS, CN or $R^3$—$A^3$—$Z^2$, and $R^3$ is alkyl having 2-15C atoms wherein one or two non-adjacent $CH_2$ groups can also be replaced by —O—, —CO—, —O—CO—, —CO—O— and/or —CH=CH—, or is F, Cl, Br, NCS or CN, and to a process for the preparation of compounds of the formula I which comprises treating with a reducing agent a compound which otherwise corresponds to the formula I, but contains one or more reducible groups and/or C—C bonds instead of H atoms, or in cyclizing a dihydroxyorganoborane or a dihalogenoorganoborane by means of 1,3-diaminopropane, 1,3-dihydroxypropane, 1,3-dimercaptopropane, 1-hydroxy-3-aminopropane, 1-hydroxy-2-mercaptopropane or 1-amino-3-mercaptopropane each of which is substituted in the 2-position, or in reacting a 2-halogeno-1,3,2-diheteraborane with an organometallic compound, or in transesterifying a di-lower alkoxyborane with 1,3-propanediol which is substituted in the 2-position, or, in order to prepare compounds of the formula I wherein $R^1$ and/or $R^2$ and/or $R^3$ are F, Cl, Br or CN, in replacing the diazonium group in a corresponding diazonium salt by F, Cl, Br or CN, or, in order to prepare esters of the formula I (wherein $Z^1$ and/or $Z^2$ are —CO—O— or —O—CO— and/or $R^1$ and/or $R^2$ and/or $R^3$ contain a carboxyl group), in reacting a corresponding carboxylic acid or one of its reactive derivatives with a corresponding alcohol or one of its reactive derivatives, or, in order to prepare nitriles of the formula I (wherein $R^1$ and/or $R^2$ and/or $R^3$ are CN and/or wherein $A^2$ and/or $A^3$ and/or $A^4$ are substituted by at least one CN group), in dehydrating the corresponding carboxamide or reacting a corresponding carboxylic acid halide with sulphamide, or, in order to prepare ethers of the formula I (wherein $R^1$ and/or $R^2$ and/or $R^3$ are an alkoxy group and/or $Z^1$ and/or $Z^2$ are —OCH$_2$— or —CH$_2$O— groups), in etherifying a corresponding hydroxy compound, and/or, if appropriate, in reacting a chlorine or bromine compound of the formula I (wherein $R^1$ and/or $R^2$ and/or $R^3$ are Cl or Br and/or wherein $A^2$ and/or $A^3$ and/or $A^4$ are substituted by at least one chlorine or bromine atom) with a cyanide, and/or, if appropriate, converting a base of the formula I into one of its acid addition salts by treatment with an acid, or, if appropriate, liberating a compound of the formula I from one of its acid addition salts by treatment with a base.

The invention also relates to liquid-crystal phases containing at least one compound having the structural element 1,3,2-dioxaborinane-2,5-diyl, 1,3,2-dithiaborinane-2,5-diyl, 1,3,2-diazaborinane-2,5-diyl, 2,5-dihydro-1,3,2-diazaborine-2,5-diyl, 1,3,2-oxazaborinane-2,5-diyl, 2,5-dihydro-6H-1,3,2-oxazaborine-2,5-diyl, 2,5-dihydro-6H-1,3,2-thiazaborine-2,5-diyl, 1,3,2-thiazaborinane-2,5-diyl or 2,3,4,5-tetrahydro-1,3,2-diazaborine-2,5-diyl, in particular a compound of the formula I, and to liquid-crystal display elements containing phases of this type. Phases of this type have particularly advantageous elastic constants. In the preceding and following text $R^1$, $R^2$, $R^3$, $A^1$, $A^2$, $A^3$, $A^4$, A, M, N, Z, $Z^1$, $Z^2$ and Y have the meaning indicated, unless anything to the contrary is expressly noted.

DETAILED DISCUSSION

The compounds of the formula I accordingly embrace compounds having two rings of the partial formulae Ia and Ib:

compounds having three rings of the partial formulae Ic to Il:

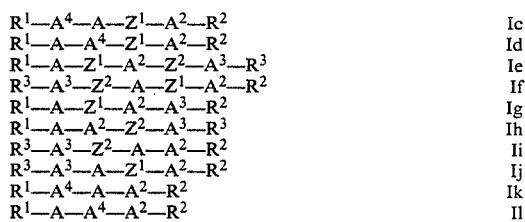

compounds having four rings of the partial formulae Im to Iff:

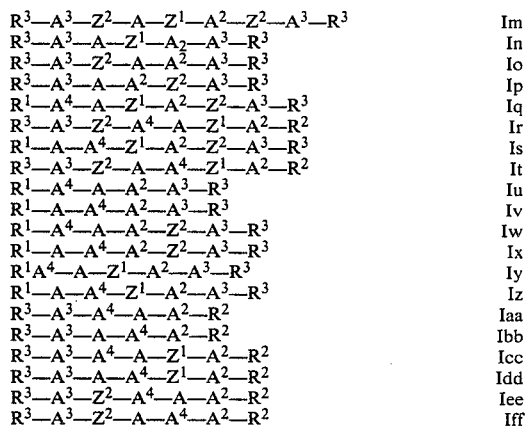

and compounds having five rings of the partial formulae Igg to Ill:

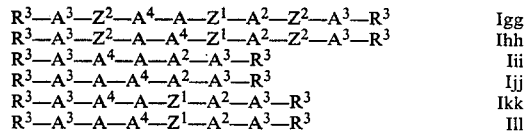

In the compounds of the preceding and following formulae, $R^1$, $R^2$ and $R^3$ are preferably alkyl and also alkoxy. In certain instances above the symbol "$R^3$" is used to indicate a preferred subgenera for $R^1$ and/or $R^2$, the meaning of $R^3$ being as above.

Compounds which are also preferred are those of the preceding and following formulae in which one of the radicals $R^1$, $R^2$ and $R^3$ is CN, F or Cl.

$A^2$, $A^3$ and $A^4$ are preferably Cy, Phe, Dio or Pyr, and also preferably OBO, OBS, OBN, OBNH, SBS, SBN, SBNH, NBN, NBNH or NHBNH; the compound of the formula I preferably does not contain more than one of the radicals OBO, OBS, OBN, OBNH, SBS, SBN, SBNH, NBN, NBNH or NHBNH or Dio, Dit, Pip, Bi, Pyn or Pyr, respectively. The Zs are preferably identical and are —CH$_2$O—, —CH$_2$S— and —CH$_2$NH—, especially —CH$_2$O—.

$Z^1$ and $Z^2$ are preferably single bonds or, as a second preference, —CO—O—, —O—CO— or —CH$_2$CH$_2$— groups. Y is preferably H or, as a second preference, —CN or —CH$_3$. M and N are preferably —CH$_2$—.

$R^3$ is preferably an alkyl group having 1–10C atoms or CN.

If $R^1$ and/or $R^2$ are alkyl radicals and/or alkoxy radicals, they can be linear or branched. Preferably, they are linear, have 2, 3, 4, 5, 6 or 7C atoms and accordingly are preferably ethyl, propyl, butyl, pentyl, hexyl, heptyl, ethoxy, propoxy, butoxy, pentoxy, hexyloxy or heptyloxy, and also methyl, octyl, nonyl, decyl, undecyl, dodecyl, tridecyl, tetradecyl, pentadecyl, methoxy, octyloxy, nonyloxy, decyloxy, undecyloxy, dodecyloxy, tridecyloxy or tetradecyloxy. In particular, they have 3–7C atoms.

Compounds of formula I with branched wing groups $R^1$ or $R^2$ or $R^3$ are of importance owing to improved solubility in the customary liquid-crystal base materials, but are of especial importance as chiral doping substances, if they are optically active. Compounds of this type can be used as components of smectic mixtures having ferro-electric properties.

Branched groups of this type as a rule contain not more than one chain branching. Preferred branched radicals $R^1$ and $R^2$ are isopropyl, 2-butyl (=1-methylpropyl), isobutyl (=2-methylpropyl), 2-methylbutyl, isopentyl (=3-methylbutyl), 2-methylpentyl, 3-methylpentyl, 2-ethylhexyl, 2-propylpentyl, isopropoxy, 2-methoxypropoxy, 2-methylbutoxy, 3-methylbutoxy, 2-methylpentoxy, 3-methylpentoxy, 2-ethylhexyloxy, 1-methylhexyloxy or 1-methylheptyloxy.

Formula I embraces both the racemates of these compounds and the optical antipodes and also mixtures thereof.

Preferably, in a 1,4-phenylene group one or two CH groups can be replaced by N.

Among the compounds of the formulae I and also Ia to Ill, preferred compounds are those in which at least one of the radicals contained therein has one of the preferred meanings indicated. Minor groups of compounds which are particularly preferred are those of the formulae I1 to I190:

| | |
|---|---|
| $R^1$—OBO—COO—Phe—$R^2$ | I1 |
| $R^1$—OBO—CH$_2$CH$_2$—Phe—$R^2$ | I2 |
| $R^1$—OBO—Phe—COO—Phe—$R^2$ | I3 |
| $R^1$—OBO—Phe—CH$_2$CH$_2$—Phe—$R^2$ | I4 |
| $R^1$—OBO—Phe—CH$_2$CH$_2$—Cy—$R^2$ | I5 |
| $R^1$—OBO—Phe—CH$_2$CH$_2$—Phe—Cy—$R^3$ | I6 |
| $R^1$—OBO—Phe—CH$_2$CH$_2$—Phe—Dio—$R^3$ | I7 |
| $R^1$—OBO—Phe—$R^2$ | I8 |
| $R^1$—OBO—Phe—Phe—$R^2$ | I9 |
| $R^1$—OBO—Phe—Phe—Cy—$R^3$ | I10 |
| $R^1$—OBO—Phe—Phe—Dio—$R^3$ | I11 |
| $R^1$—OBO—Cy—Phe—$R^2$ | I12 |
| $R^1$—Cy—OBO—Phe—$R^2$ | I13 |
| $R^1$—OBO—Cy—$R^3$ | I14 |
| $R^1$—OBO—Cy—Cy—$R^3$ | I15 |
| $R^1$—OBO—Pyr—$R^2$ | I16 |
| $R'$—OBO—CH$_2$CH$_2$—Phe—Phe—$R^2$ | I17 |
| $R^1$—OBO—CH$_2$CH$_2$—Phe—Phe—Cy—$R^3$ | I18 |
| $R^1$—OBO—CH$_2$CH$_2$—Phe—Cy—$R^2$ | I19 |
| $R^1$—OBS—COO—Phe—$R^2$ | I20 |
| $R^1$—OBS—CH$_2$CH$_2$—Phe—$R^2$ | I21 |
| $R^1$—OBS—Phe—COO—Phe—$R^2$ | I22 |
| $R^1$—OBS—Phe—CH$_2$CH$_2$—Phe—$R^2$ | I23 |
| $R^1$—OBS—Phe—CH$_2$CH$_2$—Cy—$R^2$ | I24 |
| $R^1$—OBS—Phe—CH$_2$CH$_2$—Phe—Cy—$R^3$ | I25 |
| $R^1$—OBS—Phe—CH$_2$CH$_2$—Phe—Dio—$R^3$ | I26 |
| $R^1$—OBS—Phe—$R^2$ | I27 |
| $R^1$—OBS—Phe—Phe—$R^2$ | I28 |
| $R^1$—OBS—Phe—Phe—Cy—$R^3$ | I29 |
| $R^1$—OBS—Phe—Phe—Dio—$R^3$ | I30 |
| $R^1$—OBS—Cy—Phe—$R^2$ | I31 |
| $R^1$—Cy—OBS—Phe—$R^2$ | I32 |
| $R^1$—OBS—Cy—$R^3$ | I33 |
| $R^1$—OBS—Cy—Cy—$R^3$ | I34 |
| $R^1$—OBS—Pyr—$R^2$ | I35 |
| $R^1$—OBS—CH$_2$CH$_2$—Phe—Phe—$R^2$ | I36 |
| $R^1$—OBS—CH$_2$CH$_2$—Phe—Phe—Cy—$R^3$ | I37 |
| $R^1$—OBS—CH$_2$CH$_2$—Phe—Cy—$R^2$ | I38 |
| $R^1$—OBN—COO—Phe—$R^2$ | I39 |
| $R^1$—OBN—CH$_2$CH$_2$—Phe—$R^2$ | I40 |
| $R^1$—OBN—Phe—COO—Phe—$R^2$ | I41 |
| $R^1$—OBN—Phe—CH$_2$CH$_2$—Phe—$R^2$ | I42 |
| $R^1$—OBN—Phe—CH$_2$CH$_2$—Cy—$R^2$ | I43 |
| $R^1$—OBN—Phe—CH$_2$CH$_2$—Phe—Cy—$R^3$ | I44 |
| $R^1$—OBN—Phe—CH$_2$CH$_2$—Phe—Dio—$R^3$ | I45 |
| $R^1$—OBN—Phe—$R^2$ | I46 |
| $R^1$—OBN—Phe—Phe—$R^2$ | I47 |
| $R^1$—OBN—Phe—Phe—Cy—$R^3$ | I48 |
| $R^1$—OBN—Phe—Phe—Dio—$R^3$ | I49 |
| $R^1$—OBN—Cy—Phe—$R^2$ | I50 |
| $R^1$—Cy—OBN—Phe—$R^2$ | I51 |
| $R^1$—OBN—Cy—$R^3$ | I52 |
| $R^1$—OBN—Cy—Cy—$R^3$ | I53 |
| $R^1$—OBN—Pyr—$R^2$ | I54 |
| $R^1$—OBN—CH$_2$CH$_2$—Phe—Phe—$R^2$ | I55 |
| $R^1$—OBN—CH$_2$CH$_2$—Phe—Phe—Cy—$R^3$ | I56 |
| $R^1$—OBN—CH$_2$CH$_2$—Phe—Cy—$R^2$ | I57 |
| $R^1$—OBNH—COO—Phe—$R^2$ | I58 |
| $R^1$—OBNH—CH$_2$CH$_2$—Phe—$R^2$ | I59 |
| $R^1$—OBNH—Phe—COO—Phe—$R^2$ | I60 |
| $R^1$—OBNH—Phe—CH$_2$CH$_2$—Phe—$R^2$ | I61 |
| $R^1$—OBNH—Phe—CH$_2$CH$_2$—Cy—$R^2$ | I62 |
| $R^1$—OBNH—Phe—CH$_2$CH$_2$—Phe—Cy—$R^3$ | I63 |
| $R^1$—OBNH—Phe—CH$_2$CH$_2$—Phe—Dio—$R^3$ | I64 |
| $R^1$—OBNH—Phe—$R^2$ | I65 |
| $R^1$—OBNH—Phe—Phe—$R^2$ | I66 |
| $R^1$—OBNH—Phe—Phe—Cy—$R^3$ | I67 |
| $R^1$—OBNH—Phe—Phe—Dio—$R^3$ | I68 |
| $R^1$—OBNH—Cy—Phe—$R^2$ | I69 |
| $R^1$—Cy—OBNH—Phe—$R^2$ | I70 |
| $R^1$—OBNH—Cy—$R^3$ | I71 |
| $R^1$—OBNH—Cy—Cy—$R^3$ | I72 |
| $R^1$—OBNH—Pyr—$R^2$ | I73 |
| $R^1$—OBNH—CH$_2$CH$_2$—Phe—Phe—$R^2$ | I74 |
| $R^1$—OBNH—CH$_2$CH$_2$—Phe—Phe—Cy—$R^3$ | I75 |
| $R^1$—OBNH—CH$_2$CH$_2$—Phe—Cy—$R^2$ | I76 |
| $R^1$—SBS—COO—Phe—$R^2$ | I77 |
| $R^1$—SBS—CH$_2$CH$_2$—Phe—$R^2$ | I78 |
| $R^1$—SBS—Phe—COO—Phe—$R^2$ | I79 |
| $R^1$—SBS—Phe—CH$_2$CH$_2$—Phe—$R^2$ | I80 |
| $R^1$—SBS—Phe—CH$_2$CH$_2$—Cy—$R^2$ | I81 |
| $R^1$—SBS—Phe—CH$_2$CH$_2$—Phe—Cy—$R^3$ | I82 |
| $R^1$—SBS—Phe—CH$_2$CH$_2$—Phe—Dio—$R^3$ | I83 |
| $R^1$—SBS—Phe—$R^2$ | I84 |
| $R^1$—SBS—Phe—Phe—$R^2$ | I85 |
| $R^1$—SBS—Phe—Phe—Cy—$R^3$ | I86 |
| $R^1$—SBS—Phe—Phe—Dio—$R^3$ | I87 |
| $R^1$—SBS—Cy—Phe—$R^2$ | I88 |
| $R^1$—Cy—SBS—Phe—$R^2$ | I89 |
| $R^1$—SBS—Cy—$R^3$ | I90 |
| $R^1$—SBS—Cy—Cy—$R^3$ | I91 |
| $R^1$—SBS—Pyr—$R^2$ | I92 |
| $R^1$—SBS—CH$_2$CH$_2$—Phe—Phe—$R^2$ | I93 |
| $R^1$—SBS—CH$_2$CH$_2$—Phe—Phe—Cy—$R^3$ | I94 |
| $R^1$—SBS—CH$_2$CH$_2$—Phe—Cy—$R^2$ | I95 |
| $R^1$—SBN—COO—Phe—$R^2$ | I96 |
| $R^1$—SBN—CH$_2$CH$_2$—Phe—$R^2$ | I97 |
| $R^1$—SBN—Phe—COO—Phe—$R^2$ | I98 |
| $R^1$—SBN—Phe—CH$_2$CH$_2$—Phe—$R^2$ | I99 |
| $R^1$—SBN—Phe—CH$_2$CH$_2$—Cy—$R^2$ | I100 |
| $R^1$—SBN—Phe—CH$_2$CH$_2$—Phe—Cy—$R^3$ | I101 |
| $R^1$—SBN—Phe—CH$_2$CH$_2$—Phe—Dio—$R^3$ | I102 |
| $R^1$—SBN—Phe—$R^2$ | I103 |
| $R^1$—SBN—Phe—Phe—$R^2$ | I104 |
| $R^1$—SBN—Phe—Phe—Cy—$R^3$ | I105 |
| $R^1$—SBN—Phe—Phe—Dio—$R^3$ | I106 |
| $R^1$—SBN—Cy—Phe—$R^2$ | I107 |
| $R^1$—Cy—SBN—Phe—$R^2$ | I108 |
| $R^1$—SBN—Cy—$R^3$ | I109 |
| $R^1$—SBN—Cy—Cy—$R^3$ | I110 |

R¹—SBN—Pyr—R²
R¹—SBN—CH₂CH₂—Phe—Phe—R²
R¹—SBN—CH₂CH₂—Phe—Phe—Cy—R³
R¹—SBN—CH₂CH₂—Phe—Cy—R²
R¹—SBNH—COO—Phe—R²
R¹—SBNH—CH₂CH₂—Phe—R²
R¹—SBNH—Phe—COO—Phe—R²
R¹—SBNH—Phe—CH₂CH₂—Phe—R²
R¹—SBNH—Phe—CH₂CH₂—Cy—R²
R¹—SBNH—Phe—CH₂CH₂—Phe—Cy—R³
R¹—SBNH—Phe—CH₂CH₂—Phe—Dio—R³
R¹—SBNH—Phe—R²
R¹—SBNH—Phe—Phe—R²
R¹—SBNH—Phe—Cy—R³
R¹—SBNH—Phe—Phe—Dio—R³
R¹—SBNH—Cy—Phe—R²
R¹—Cy—SBNH—Phe—R²
R¹—SBNH—Cy—R³
R¹—SBNH—Cy—Cy—R³
R¹—SBNH—Pyr—R²
R¹—SBNH—CH₂CH₂—Phe—Phe—R²
R¹—SBNH—CH₂CH₂—Phe—Phe—Cy—R³
R¹—SBNH—CH₂CH₂—Phe—Cy—R²
R¹—NBN—COO—Phe—R²
R¹—NBN—CH₂CH₂—Phe—R²
R¹—NBN—Phe—COO—Phe—R²
R¹—NBN—Phe—CH₂CH₂—Phe—R²
R¹—NBN—Phe—CH₂CH₂—Cy—R²
R¹—NBN—Phe—CH₂CH₂—Phe—Cy—R³
R¹—NBN—Phe—CH₂CH₂—Phe—Dio—R³
R¹—NBN—Phe—R²
R¹—NBN—Phe—Phe—R²
R¹—NBN—Phe—Phe—Cy—R³
R¹—NBN—Phe—Phe—Dio—R³
R¹—NBN—Cy—Phe—R²
R¹—Cy—NBN—Phe—R²
R¹—NBN—Cy—R³
R¹—NBN—Cy—Cy—R³
R¹—NBN—Pyr—R²
R¹—NBN—CH₂CH₂—Phe—Phe—R²
R¹—NBN—CH₂CH₂—Phe—Phe—Cy—R³
R¹—NBN—CH₂CH₂—Phe—Cy—R²
R¹—NBNH—COO—Phe—R²
R¹—NBNH—CH₂CH₂—Phe—R²
R¹—NBNH—Phe—COO—Phe—R²
R¹—NBNH—Phe—CH₂CH₂—Phe—R²
R¹—NBNH—Phe—CH₂CH₂—Cy—R²
R¹—NBNH—Phe—CH₂CH₂—Phe—Cy—R³
R¹—NBNH—Phe—CH₂Ch₂—Phe—Dio—R³
R¹—NBNH—Phe—R²
R¹—NBNH—Phe—Phe—R²
R¹—NBNH—Phe—Phe—Cy—R³
R¹—NBNH—Phe—Phe—Dio—R³
R¹—NBNH—Cy—Phe—R²
R¹—Cy—NBNH—Phe—R²
R¹—NBNH—Cy—R³
R¹—NBNH—Cy—Cy—R³
R¹—NBNH—Pyr—R²
R¹—NBNH—CH₂CH₂—Phe—Phe—R²
R¹—NBNH—CH₂CH₂—Phe—Phe—Cy—R³
R¹—NBNH—CH₂CH₂—Phe—Cy—R²
R¹—NHBNH—COO—Phe—R²
R¹—NHBNH—CH₂CH₂—Phe—R²
R¹—NHBNH—Phe—COO—Phe—R²
R¹—NHBNH—Phe—CH₂CH₂—Phe—R²
R¹—NHBNH—Phe—CH₂CH₂—Cy—R²
R¹—NHBNH—Phe—CH₂CH₂—Phe—Cy—R³
R¹—NHBNH—Phe—CH₂CH₂—Phe—Dio—R³
R¹—NHBNH—Phe—R²
R¹—NHBNH—Phe—Phe—R²
R¹—NHBNH—Phe—Phe—Cy—R³
R¹—NHBNH—Phe—Phe—Dio—R³
R¹—NHBNH—Cy—Phe—R²
R¹—Cy—NHBNH—Phe—R²
R¹—NHBNH—Cy—R³
R¹—NHBNH—Cy—Cy—R³
R¹—NHBNH—Pyr—R²
R¹—NHBNH—CH₂CH₂—Phe—Phe—R²
R¹—NHBNH—CH₂CH₂—Phe—Phe—Cy—R³
R¹—NHBNH—CH₂CH₂—Phe—Cy—R²

Preferred stereoisomers in the compounds of the formula I are those in which the rings Cy, Dio, Dit and/or Pip are disubstituted in the trans-1,4-position.

Those compounds of the formulae mentioned above which contain one or more groups OBO, OBS, OBN, OBNH, SBS, SBNH, NBN, NBNH, NHBNH, Dio, Dit, Pip and/or Pyr embrace the two possible 2,5-position isomers (OBO, OBS, OBN, OBNH, SBS, SBN, SBNH, NBN, NBNH, NHBNH, Dio, Dit or Pyr) or 1,4-position isomers (Pip), respectively.

In the compounds of the formula I in which $A^1$ is a ring OBO, OBS, OBN, OBNH, SBS, SBN, SBNH, NBN, NBNH or NHBNH which is substituted in the 2-position by $R^1$, $R^1$ is preferably alkyl.

Compounds of the formula I which are particularly preferred are those wherein $R^1$ and $R^2$ are each linear or not more than singly branched alkyl groups or alkoxy groups having 1–10 C atoms or CN.

The following minor groups of compounds in which —A— is 1,3,2-dioxaborinane-2,5-diyl, 1,3,2-dithiaborinane-2,5-diyl, 1,3,2-diazaborinane-2,5-diyl, 2,5-dihydro-1,3,2-diazaborine-2,5-diyl, 1,3,2-oxazaborinane-2,5-diyl, 2,5-dihydro-6H-1,3,2-oxazaborine-2,5-diyl, 2,5-dihydro-6H-1,3,2-thiazaborine-2,5-diyl, 2,3,4,5-tetrahydro-1,3,2-diazaborine-2,5-diyl, 1,3,2-thiazaborinane-2,5-diyl or 1,3,2-oxathiaborinane-2,5-diyl, Phe is 1,4-phenylene, Cyc is 1,4-cyclohexylene, Dio is 1,3-dioxane-2,5-diyl and Pyr is pyrimidine-2,5-diyl are particularly preferred.

Alkyl is preferably linear methyl, ethyl, propyl, butyl, pentyl, hexyl, heptyl, octyl, nonyl or decyl; oxaalkyl is preferably linear 2-oxapropyl (=methoxymethyl), 2-oxabutyl (=ethoxymethyl) or 3-oxabutyl (=2-methoxyethyl), 2-, 3- or 4-oxapentyl, 2-, 3-, 4- or 5-oxahexyl, 2-, 3-, 4-, 5- or 6-oxaheptyl, 2-, 3-, 4-, 5-, 6- or 7-oxaoctyl, 2-, 3, 4-, 5-, 6-, 7- or 8-oxanonyl or 2-, 3-, 4-, 5-, 6-, 7-, 8- or 9-oxadecyl.

Other preferred compounds of this invention are:
I.
　Alkyl—A—Phe—CN
　Alkyl—A—Phe—Methyl
　Alkyl—A—Phe—Ethyl
　Alkyl—A—Phe—Propyl
　Alkyl—A—Phe—Butyl
　Alkyl—A—Phe—Pentyl
　Alkyl—A—Phe—Hexyl
　Alkyl—A—Phe—Heptyl
　Alkyl—A—Phe—Octyl
　Alkyl—A—Phe—Nonyl
　Alkyl—A—Phe—Decyl
II.
　Alkyl—A—Phe—Methoxy
　Alkyl—A—Phe—Ethoxy
　Alkyl—A—Phe—Propoxy
　Alkyl—A—Phe—Butoxy
　Alkyl—A—Phe—Pentoxy
　Alkyl—A—Phe—Hexyloxy
　Alkyl—A—Phe—Heptyloxy
　Alkyl—A—Phe—Octyloxy
　Alkyl—A—Phe—Nonyloxy
　Alkyl—A—Phe—Decyloxy
　Alkyl—A—(3—F—Phe)—CN
III.
　Alkyl—A—Cyc—CN
　Alkyl—A—Cyc—Methyl
　Alkyl—A—Cyc—Ethyl
　Alkyl—A—Cyc—Propyl
　Alkyl—A—Cyc—Butyl
　Alkyl—A—Cyc—Pentyl
　Alkyl—A—Cyc—Hexyl
　Alkyl—A—Cyc—Heptyl Alkyl—A—Cyc—Octyl
Alkyl—A—Cyc—Nonyl
Alkyl—A—Cyc—Decyl IV.
Alkyl—A—Cyc—Methoxy
Alkyl—A—Cyc—Ethoxy
Alkyl—A—Cyc—Propoxy
Alkyl—A—Cyc—Butoxy
Alkyl—A—Cyc—Pentoxy
Alkyl—A—Cyc—Hexyloxy
Alkyl—A—Cyc—Heptyloxy
Alkyl—A—Cyc—Octyloxy
Alkyl—A—Cyc—Nonyloxy
Alkyl—A—Cyc—Decyloxy V.
Alkyl—A—Cyc—Methoxycarbonyl
Alkyl—A—Cyc—Ethoxycarbonyl
Alkyl—A—Cyc—Propoxycarbonyl
Alkyl—A—Cyc—Butoxycarbonyl
Alkyl—A—Cyc—Pentoxycarbonyl
Alkyl—A—Cyc—Hexyloxycarbonyl
Alkyl—A—Cyc—Heptyloxycarbonyl
Alkyl—A—Cyc—Octyloxycarbonyl
Alkyl—A—Cyc—Nonyloxycarbonyl
Alkyl—A—Cyc—Decyloxycarbonyl VI.
Alkyl—A—Cyc—Methylcarbonyloxy
Alkyl—A—Cyc—Ethylcarbonyloxy
Alkyl—A—Cyc—Propylcarbonyloxy
Alkyl—A—Cyc—Butylcarbonyloxy
Alkyl—A—Cyc—Pentylcarbonyloxy
Alkyl—A—Cyc—Hexylcarbonyloxy
Alkyl—A—Cyc—Heptylcarbonyloxy
Alkyl—A—Cyc—Octylcarbonyloxy
Alkyl—A—Cyc—Nonylcarbonyloxy
Alkyl—A—Cyc—Decylcarbonyloxy VII.
Methyl—A—Cyc—Oxaalkyl
Ethyl—A—Cyc—Oxaalkyl
Propyl—A—Cyc—Oxaalkyl
Butyl—A—Cyc—Oxaalkyl
Pentyl—A—Cyc—Oxaalkyl
Hexyl—A—Cyc—Oxaalkyl
Heptyl—A—Cyc—Oxaalkyl
Octyl—A—Cyc—Oxaalkyl
Nonyl—A—Cyc—Oxaalkyl
Decyl—A—Cyc—Oxaalkyl VIII.
Alkyl—A—Phe—Phe—CN
Alkyl—A—Phe—Phe—Methyl
Alkyl—A—Phe—Phe—Ethyl
Alkyl—A—Phe—Phe—Propyl
Alkyl—A—Phe—Phe—Butyl
Alkyl—A—Phe—Phe—Pentyl
Alkyl—A—Phe—Phe—Hexyl
Alkyl—A—Phe—Phe—Heptyl
Alkyl—A—Phe—Phe—Octyl
Alkyl—A—Phe—Phe—Nonyl
Alkyl—A—Phe—Phe—Decyl
Alkyl—A—Phe(3—F—Phe)—CN IX.
Alkyl—A—Phe—Phe—Methoxy
Alkyl—A—Phe—Phe—Ethoxy
Alkyl—A—Phe—Phe—Propoxy
Alkyl—A—Phe—Phe—Butoxy
Alkyl—A—Phe—Phe—Pentoxy
Alkyl—A—Phe—Phe—Hexyloxy
Alkyl—A—Phe—Phe—Heptyloxy
Alkyl—A—Phe—Phe—Octyloxy
Alkyl—A—Phe—Phe—Nonyloxy
Alkyl—A—Phe—Phe—Decyloxy X.
Alkyl—A—Cyc—Phe—CN
Alkyl—A—Cyc—Phe—Methyl
Alkyl—A—Cyc—Phe—Ethyl
Alkyl—A—Cyc—Phe—Propyl
Alkyl—A—Cyc—Phe—Butyl
Alkyl—A—Cyc—Phe—Pentyl
Alkyl—A—Cyc—Phe—Hexyl
Alkyl—A—Cyc—Phe—Heptyl
Alkyl—A—Cyc—Phe—Octyl
Alkyl—A—Cyc—Phe—Nonyl
Alkyl—A—Cyc—Phe—Decyl
Alkyl—A—Cyc—(3—F—Phe)—CN XI.
Alkyl—A—Cyc—Phe—Methoxy
Alkyl—A—Cyc—Phe—Ethoxy
Alkyl—A—Cyc—Phe—Propoxy
Alkyl—A—Cyc—Phe—Butoxy
Alkyl—A—Cyc—Phe—Pentoxy
Alkyl—A—Cyc—Phe—Hexyloxy
Alkyl—A—Cyc—Phe—Heptyloxy
Alkyl—A—Cyc—Phe—Octyloxy
Alkyl—A—Cyc—Phe—Nonyloxy
Alkyl—A—Cyc—Phe—Decyloxy XII.
Alkyl—A—Cyc—Cyc—CN
Alkyl—A—Cyc—Cyc—Methyl
Alkyl—A—Cyc—Cyc—Ethyl
Alkyl—A—Cyc—Cyc—Propyl
Alkyl—A—Cyc—Cyc—Butyl
Alkyl—A—Cyc—Cyc—Pentyl
Alkyl—A—Cyc—Cyc—Hexyl
Alkyl—A—Cyc—Cyc—Heptyl
Alkyl—A—Cyc—Cyc—Octyl
Alkyl—A—Cyc—Cyc—Nonyl
Alkyl—A—Cyc—Cyc—Decyl XIII.
Alkyl—Cyc—A—Phe—CN
Alkyl—Cyc—A—Phe—Methyl
Alkyl—Cyc—A—Phe—Ethyl
Alkyl—Cyc—A—Phe—Propyl
Alkyl—Cyc—A—Phe—Butyl
Alkyl—Cyc—A—Phe—Pentyl
Alkyl—Cyc—A—Phe—Hexyl
Alkyl—Cyc—A—Phe—Heptyl
Alkyl—Cyc—A—Phe—Octyl
Alkyl—Cyc—A—Phe—Nonyl
Alkyl—Cyc—A—Phe—Decyl
Alkyl—Cyc—A—(3—F—Phe)—CN XIV.
Alkyl—Cyc—A—Phe—Methoxy
Alkyl—Cyc—A—Phe—Ethoxy
Alkyl—Cyc—A—Phe—Propoxy
Alkyl—Cyc—A—Phe—Butoxy
Alkyl—Cyc—A—Phe—Pentoxy
Alkyl—Cyc—A—Phe—Hexyloxy
Alkyl—Cyc—A—Phe—Heptyloxy
Alkyl—Cyc—A—Phe—Octyloxy
Alkyl—Cyc—A—Phe—Nonyloxy
Alkyl—Cyc—A—Phe—Decyloxy XV.
Cyan—Cyc—Phe—Phe—A—Alkyl
Methyl—Cyc—Phe—Phe—A—Alkyl
Ethyl—Cyc—Phe—Phe—A—Alkyl
Propyl—Cyc—Phe—Phe—A—Alkyl Butyl—Cyc—Phe—Phe—A—Alkyl
Pentyl—Cyc—Phe—Phe—A—Alkyl
Hexyl—Cyc—Phe—Phe—A—Alkyl
Heptyl—Cyc—Phe—Phe—A—Alkyl
Octyl—Cyc—Phe—Phe—A—Alkyl
Nonyl—Cyc—Phe—Phe—A—Alkyl
Decyl—Cyc—Phe—Phe—A—Alkyl XVI.
Alkyl—A—Pyr—Methyl
Alkyl—A—Pyr—Ethyl
Alkyl—A—Pyr—Propyl
Alkyl—A—Pyr—Butyl
Alkyl—A—Pyr—Pentyl
Alkyl—A—Pyr—Hexyl
Alkyl—A—Pyr—Heptyl
Alkyl—A—Pyr—Octyl
Alkyl—A—Pyr—Nonyl
Alkyl—A—Pyr—Decyl XVII.
Alkyl—A—Pyr—Phe—CN XVIII.
Alkyl—A—OCO—Phe—CN
Alkyl—A—OCO—Phe—Methyl
Alkyl—A—OCO—Phe—Ethyl
Alkyl—A—OCO—Phe—Propyl
Alkyl—A—OCO—Phe—Butyl
Alkyl—A—OCO—Phe—Pentyl
Alkyl—A—OCO—Phe—Hexyl
Alkyl—A—OCO—Phe—Heptyl
Alkyl—A—OCO—Phe—Octyl
Alkyl—A—OCO—Phe—Nonyl
Alkyl—A—OCO—Phe—Decyl XIX.
Alkyl—A—OCO—Phe—Methoxy
Alkyl—A—OCO—Phe—Ethoxy
Alkyl—A—OCO—Phe—Propoxy
Alkyl—A—OCO—Phe—Butoxy
Alkyl—A—OCO—Phe—Pentoxy
Alkyl—A—OCO—Phe—Hexyloxy
Alkyl—A—OCO—Phe—Heptyloxy
Alkyl—A—OCO—Phe—Octyloxy
Alkyl—A—OCO—Phe—Nonyloxy
Alkyl—A—OCO—Phe—Decyloxy XX.
Alkyl—A—OCO—Cyc—CN
Alkyl—A—OCO—Cyc—Methyl
Alkyl—A—OCO—Cyc—Ethyl
Alkyl—A—OCO—Cyc—Propyl
Alkyl—A—OCO—Cyc—Butyl
Alkyl—A—OCO—Cyc—Pentyl
Alkyl—A—OCO—Cyc—Hexyl
Alkyl—A—OCO—Cyc—Heptyl
Alkyl—A—OCO—Cyc—Octyl
Alkyl—A—OCO—Cyc—Nonyl
Alkyl—A—OCO—Cyc—Decyl XXI.
Alkyl—A—OCO—Phe—Phe—CN
Alkyl—A—OCO—Phe—Phe—Methyl
Alkyl—A—OCO—Phe—Phe—Ethyl
Alkyl—A—OCO—Phe—Phe—Propyl
Alkyl—A—OCO—Phe—Phe—Butyl
Alkyl—A—OCO—Phe—Phe—Pentyl
Alkyl—A—OCO—Phe—Phe—Hexyl
Alkyl—A—OCO—Phe—Phe—Heptyl
Alkyl—A—OCO—Phe—Phe—Octyl
Alkyl—A—OCO—Phe—Phe—Nonyl
Alkyl—A—OCO—Phe—Phe—Decyl XXII.
Alkyl—A—Phe—COO—Cyc—CN
Alkyl—A—Phe—COO—Cyc—Methyl
Alkyl—A—Phe—COO—Cyc—Ethyl
Alkyl—A—Phe—COO—Cyc—Propyl
Alkyl—A—Phe—COO—Cyc—Butyl
Alkyl—A—Phe—COO—Cyc—Pentyl
Alkyl—A—Phe—COO—Cyc—Hexyl
Alkyl—A—Phe—COO—Cyc—Heptyl
Alkyl—A—Phe—COO—Cyc—Octyl
Alkyl—A—Phe—COO—Cyc—Nonyl
Alkyl—A—Phe—COO—Cyc—Decyl XXIII.
Alkyl—A—Phe—COO—Phe—CN
Alkyl—A—Phe—COO—Phe—Methyl
Alkyl—A—Phe—COO—Phe—Ethyl
Alkyl—A—Phe—COO—Phe—Propyl
Alkyl—A—Phe—COO—Phe—Butyl
Alkyl—A—Phe—COO—Phe—Pentyl
Alkyl—A—Phe—COO—Phe—Hexyl
Alkyl—A—Phe—COO—Phe—Heptyl
Alkyl—A—Phe—COO—Phe—Octyl
Alkyl—A—Phe—COO—Phe—Nonyl
Alkyl—A—Phe—COO—Phe—Decyl XXIV.
Alkyl—A—Phe—COO—Phe—Methoxy
Alkyl—A—Phe—COO—Phe—Ethoxy
Alkyl—A—Phe—COO—Phe—Propoxy
Alkyl—A—Phe—COO—Phe—Butoxy
Alkyl—A—Phe—COO—Phe—Pentoxy
Alkyl—A—Phe—COO—Phe—Hexyloxy
Alkyl—A—Phe—COO—Phe—Heptyloxy
Alkyl—A—Phe—COO—Phe—Octyloxy
Alkyl—A—Phe—COO—Phe—Nonyloxy
Alkyl—A—Phe—COO—Phe—Decyloxy XXV.
Alkyl—A—Phe—COO—(3—F—Phe)—CN
Alkyl—A—Phe—CH$_2$CH$_2$—(3—F—Phe)—CN
Alkyl—A—Phe—CH$_2$O—(3—F—Phe)—CN XXVI.
Alkyl—A—Cyc—COO—Cyc—CN
Alkyl—A—Cyc—COO—Cyc—Methyl
Alkyl—A—Cyc—COO—Cyc—Ethyl
Alkyl—A—Cyc—COO—Cyc—Propyl
Alkyl—A—Cyc—COO—Cyc—Butyl
Alkyl—A—Cyc—COO—Cyc—Pentyl
Alkyl—A—Cyc—COO—Cyc—Hexyl
Alkyl—A—Cyc—COO—Cyc—Heptyl
Alkyl—A—Cyc—COO—Cyc—Octyl
Alkyl—A—Cyc—COO—Cyc—Nonyl
Alkyl—A—Cyc—COO—Cyc—Decyl XXVII.
Alkyl—A—Cyc—COO—Phe—CN
Alkyl—A—Cyc—COO—Phe—Methyl
Alkyl—A—Cyc—COO—Phe—Ethyl
Alkyl—A—Cyc—COO—Phe—Propyl
Alkyl—A—Cyc—COO—Phe—Butyl
Alkyl—A—Cyc—COO—Phe—Pentyl
Alkyl—A—Cyc—COO—Phe—Hexyl
Alkyl—A—Cyc—COO—Phe—Heptyl
Alkyl—A—Cyc—COO—Phe—Octyl
Alkyl—A—Cyc—COO—Phe—Nonyl
Alkyl—A—Cyc—COO—Phe—Decyl XXVIII.
Alkyl—A—Cyc—COO—Phe—Methoxy
Alkyl—A—Cyc—COO—Phe—Ethoxy
Alkyl—A—Cyc—COO—Phe—Propoxy
Alkyl—A—Cyc—COO—Phe—Butoxy
Alkyl—A—Cyc—COO—Phe—Pentoxy Alkyl—A—Cyc—COO—Phe—Hexyloxy
Alkyl—A—Cyc—COO—Phe—Heptyloxy
Alkyl—A—Cyc—COO—Phe—Octyloxy
Alkyl—A—Cyc—COO—Phe—Nonyloxy
Alkyl—A—Cyc—COO—Phe—Decyloxy XXIX.
Alkyl—A—OCO—Dio—Methyl
Alkyl—A—OCO—Dio—Ethyl
Alkyl—A—OCO—Dio—Propyl
Alkyl—A—OCO—Dio—Butyl
Alkyl—A—OCO—Dio—Pentyl
Alkyl—A—OCO—Dio—Hexyl
Alkyl—A—OCO—Dio—Heptyl
Alkyl—A—OCO—Dio—Octyl
Alkyl—A—OCO—Dio—Nonyl
Alkyl—A—OCO—Dio—Decyl XXX.
Alkyl—A—CH$_2$CH$_2$—Phe—Phe—CN
Alkyl—A—CH$_2$CH$_2$—Phe—Phe—Methyl
Alkyl—A—CH$_2$CH$_2$—Phe—Phe—Ethyl
Alkyl—A—CH$_2$CH$_2$—Phe—Phe—Propyl
Alkyl—A—CH$_2$CH$_2$—Phe—Phe—Butyl
Alkyl—A—CH$_2$CH$_2$—Phe—Phe—Pentyl
Alkyl—A—CH$_2$CH$_2$—Phe—Phe—Hexyl
Alkyl—A—CH$_2$CH$_2$—Phe—Phe—Heptyl
Alkyl—A—CH$_2$CH$_2$—Phe—Phe—Octyl
Alkyl—A—CH$_2$CH$_2$—Phe—Phe—Nonyl
Alkyl—A—CH$_2$CH$_2$—Phe—Phe—Decyl XXXI.
Alkyl—A—CH$_2$CH$_2$—Phe—(2—F—Phe)—CN
Alkyl—A—CH$_2$CH$_2$—Phe—(2—F—Phe)—Methyl
Alkyl—A—CH$_2$CH$_2$—Phe—(2—F—Phe)—Ethyl
Alkyl—A—CH$_2$CH$_2$—Phe—(2—F—Phe)—Propyl
Alkyl—A—CH$_2$CH$_2$—Phe—(2—F—Phe)—Butyl
Alkyl—A—CH$_2$CH$_2$—Phe—(2—F—Phe)—Pentyl
Alkyl—A—CH$_2$CH$_2$—Phe—(2—F—Phe)—Hexyl
Alkyl—A—CH$_2$CH$_2$—Phe—(2—F—Phe)—Heptyl
Alkyl—A—CH$_2$CH$_2$—Phe—(2—F—Phe)—Octyl
Alkyl—A—CH$_2$CH$_2$—Phe—(2—F—Phe)—Nonyl
Alkyl—A—CH$_2$CH$_2$—Phe—(2—F—Phe)—Decyl XXXII.
Alkyl—A—CH$_2$CH$_2$—Phe—(2—F—Phe)—Methoxy
Alkyl—A—CH$_2$CH$_2$—Phe—(2—F—Phe)—Ethoxy
Alkyl—A—CH$_2$CH$_2$—Phe—(2—F—Phe)—Propoxy
Alkyl—A—CH$_2$CH$_2$—Phe—(2—F—Phe)—Butoxy
Alkyl—A—CH$_2$CH$_2$—Phe—(2—F—Phe)—Pentoxy
Alkyl—A—CH$_2$CH$_2$—Phe—(2—F—Phe)—Hexyloxy
Alkyl—A—CH$_2$CH$_2$—Phe—(2—F—Phe)—Heptyloxy
Alkyl—A—CH$_2$CH$_2$—Phe—(2—F—Phe)—Octyloxy
Alkyl—A—CH$_2$CH$_2$—Phe—(2—F—Phe)—Nonyloxy
Alkyl—A—CH$_2$CH$_2$—Phe—(2—F—Phe)—Decyloxy XXXIII.
Alkyl—A—CH$_2$O—Phe—Pyr—Methyl
Alkyl—A—CH$_2$O—Phe—Pyr—Ethyl
Alkyl—A—CH$_2$O—Phe—Pyr—Propyl
Alkyl—A—CH$_2$O—Phe—Pyr—Butyl
Alkyl—A—CH$_2$O—Phe—Pyr—Pentyl
Alkyl—A—CH$_2$O—Phe—Pyr—Hexyl
Alkyl—A—CH$_2$O—Phe—Pyr—Heptyl
Alkyl—A—CH$_2$O—Phe—Pyr—Octyl
Alkyl—A—CH$_2$O—Phe—Pyr—Nonyl
Alkyl—A—CH$_2$O—Phe—Pyr—Decyl XXXIV.
Alkyl—A—CH$_2$CH$_2$—Cyc—CN
Alkyl—A—CH$_2$CH$_2$—Cyc—Methyl
Alkyl—A—CH$_2$CH$_2$—Cyc—Ethyl
Alkyl—A—CH$_2$CH$_2$—Cyc—Propyl
Alkyl—A—CH$_2$CH$_2$—Cyc—Butyl
Alkyl—A—CH$_2$CH$_2$—Cyc—Pentyl
Alkyl—A—CH$_2$CH$_2$—Cyc—Hexyl
Alkyl—A—CH$_2$CH$_2$—Cyc—Heptyl
Alkyl—A—CH$_2$CH$_2$—Cyc—Octyl
Alkyl—A—CH$_2$CH$_2$—Cyc—Nonyl
Alkyl—A—CH$_2$CH$_2$—Cyc—Decyl The compounds of the formula I are prepared by methods which are in themselves known, such as are described in the literature (for example in the standard works such as Houben-Weyl, Methoden der Organischen Chemie ("Methods of Organic Chemistry"), Georg-Thieme-Verlag, Stuttgart), specifically under reaction conditions which are known and suitable for the reactions mentioned. In this respect it is also possible to make use of variants which are in themselves known but are not mentioned here in detail.

If desired, the starting materials can also be formed in situ in a procedure in which they are not isolated from the reaction mixture, but are immediately reacted further to give the compounds of the formula I.

Thus the compounds of the formula I can be prepared by reducing a compound which otherwise corresponds to the formula I, but contains one or more reducible groups and/or C—C bonds instead of H atoms.

Suitable reducible groups are preferably carbonyl groups, in particular keto groups, and also, for example, free or esterified hydroxyl groups or halogen atoms attached to an aromatic nucleus. Preferred starting materials for the reduction correspond to the formula I, but can contain a cyclohexene ring or cyclohexanone ring instead of a cyclohexane ring and/or a —CH=CH— group instead of a —CH$_2$CH$_2$— group and/or a —CO— group instead of a —CH$_2$— group and/or a free OH group or a functionally modified OH group (for example in the form of its p-toluenesulphonate) instead of an H atom.

The reduction can, for example, be carried out by catalytic hydrogenation at temperatures between about 0° and about 200° and pressures between about 1 and 200 bar, in an inert solvent, for example an alcohol, such as methanol, ethanol or isopropanol, an ether, such as tetrahydrofuran (THF) or dioxane, an ester, such as ethyl acetate, a carboxylic acid, such as acetic acid, or a hydrocarbon, such as cyclohexane. Suitable catalysts are preferably noble metals, such as Pt or Pd, which can be employed in the form of oxides (for example PtO$_2$ or PdO), on a support (for example Pd on charcoal, calcium carbonate or strontium carbonate) or in a finely divided form.

Ketones can also be reduced by the methods of Clemmensen (using zinc, amalgamated zinc or tin and hydrochloric acid, preferably in an aqueous alcoholic solution or in a heterogeneous phase with water/toluene at temperatures between about 80° and 120°) or of Wolff-Kishner (using hydrazine, preferably in the presence of an alkali, such as KOH or NaOH, in a high-boiling solvent, such as diethylene glycol or triethylene glycol, at temperatures between about 100° to 200°) to give the corresponding compounds of the formula I containing alkyl groups and/or —CH$_2$CH$_2$— bridges.

Reductions by means of complex hydrides are also possible. For example, arylsulphonyloxy groups can be removed reductively by means of LiAlH$_4$, in particular p-toluenesulphonyloxymethyl groups can be reduced to give methyl groups, preferably in an inert solvent, such as diethyl ether or THF, at temperatures between about 0° and 100°. Double bonds can also be hydrogenated (even in the presence of CN groups) by means of NaBH$_4$ or tributyltin hydride in methanol.

Compounds of the formula I can be cyclized particularly advantageously by the cyclization of dihydroxyorganoboranes or dihalogenoorganoboranes by means of 1,3-diaminopropane, 1,3-dihydroxypropane, 1,3-dimercaptopropane, 1-hydroxy-3-aminopropane, 1-hydroxy-3-mercaptopropane or 1-amino-3-mercaptopropane, in each case substituted in the 2-position.

1,2,3-Substituted propanes of this type are known or can be obtained by known methods. Thus, for example, alcohols can be prepared from the corresponding carboxylic acids or derivatives thereof by reduction. Mercaptans and amines can, for example, be prepared from thiuronium salts or phthalimides, which are accessible via the halides obtainable from the alcohols.

The dihydroxyorganoboranes and dihalogenoorganoboranes used as the starting materials are in part known, but for the most part are new and can be obtained by methods which are in themselves known. Dihalogenoorganoboranes can be prepared, for example, by reacting olefin or aromatic hydrocarbons with trihalogenoboranes or dihalogenohydroboranes. The reaction of iodoaromatic compounds with trihalogenoboranes is particularly suitable.

Dihydroxyorganoboranes or dialkoxyorganoboranes also afford dihalogenoorganoboranes on treatment with phosphorus(V) chloride or trihalogenoboranes.

Dihydroxyorganoboranes can be prepared from triorganoboranes by controlled hydrolysis. Trihalogenoboranes or simple trialkylboranes can be reacted with aryl Grignard compounds to give, after working up under aqueous conditions, dihydroxyarylboranes.

The reaction of trihalogenoboranes with aromatic hydrocarbons and subsequently with water also affords access to the desired compounds. The reaction of trialkoxyboranes with organometallic compounds, such as, for example, organosodium, organolithium or organomagnesium compounds, followed by working up by hydrolysis is particularly suitable for the preparation of dihydroxyorganoboranes.

The reactants are cyclized with one another in the absence of a solvent or, preferably, in the presence of an inert solvent.

Suitable diluents are preferably ethers, such as diethyl ether, dibutyl ether, tetrahydrofuran or dioxane, amides, such as dimethylformamide or hexamethylphosphoric acid triamide, hydrocarbons, such as hexane, cyclohexane, benzene, toluene or xylene, halogenated hydrocarbons, such as methylene dichloride, chloroform, carbon tetrachloride or tetrachloroethylene, sulphoxides, such as dimethyl sulphoxide, sulpholane and further organic solvents, such as acetonitrile and nitromethane. For the rection of dihydroxyorganoboranes, water-immiscible solvents can, at the same time, be advantageously used for the removal by azeotropic distillation of the water formed in the cyclocondensation. The water of reaction can also be removed by adding dehydrating agents, such as, for example, copper-(II) sulfate, sulphuric acid or a molecular sieve. The presence of a base for the removal of the hydrogen halide formed is preferable in the case of the reactions of dihalogenoorganoboranes. Examples of suitable bases are alkali metal amides, alkali and alkaline earth metal hydroxides, carbonates and bicarbonates and ammonia, strong organic bases and basic ion exchangers. The preferred bases are alkali metal hydroxides and organic bases, in particular potassium hydroxide, sodium hydroxide, pyridine and triethylamine. It is also possible, however, to react the starting materials with one another without the addition of a further reactant.

In a further advantageous process, 2-halogeno-1,3,2-diheteraboranes are reacted with an organometallic compound.

The halogenoboranes which are employed as the starting materials are obtained by metathesis in accordance with known methods, for example from triorganoboranes and trihalogenoboranes. Suitable organometallic compounds are, in particular, those of the alkali metals, such as, for example, lithium, sodium and potassium, but also other compounds, such as, for example, those of magnesium, aluminum and tin.

The reaction is advantageously carried out in the presence of an inert solvent. Solvents which are very suitable are, in particular, ethers, such as diethyl ether, tetrahydrofuran, dioxane, ethylene glycol dimethyl ether or diethylene glycol dimethyl ether, and hydrocarbons, such as hexane, cyclohexane, benzene or toluene. The reaction temperature is between −100° and +40° C., preferably between −60° and 0°. At these temperatures the reactions are, as a rule, complete after 30 minutes to 24 hours.

Finally, it is also possible to react acyclic lower dialkoxyboranes advantageously with 1,3-propanediols which are substituted in the 2-position to give compounds of the formula I.

1,3-Propanediols which are substituted in the 2-position are known or can be obtained by known methods, for example by reduction from malonic esters which are substituted in the 2-position. Lower dialkoxyboranes are obtainable, for example, from dihydroxyorganoboranes or dihalogenoorganoboranes together with alkanols in accordance with standard processes for esterification.

The reaction is carried out by transesterifying the lower dialkoxyborane and the 1,3-propanediol substituted in the 2-position without a solvent, using an excess of propanediol and/or in the presence of an inert solvent, and it is preferable to remove the lower alkanol from the reaction mixture by distillation. It is preferable to employ dimethoxyborane, diethoxyborane or diisopropoxyborane as dialkoxyboranes by virtue of the lower boiling point of the corresponding alcohols. Suitable diluents are preferably ethers, such as diethyl ether, tetrahydrofuran or dioxane, hydrocarbons, such as pentane, cyclohexane or toluene, or halogenated hydrocarbons, such as methylene dichloride, chloroform or carbon tetrachloride. The reaction temperatures are usually between 0° and the boiling point of the lowest boiling reaction component, preferably between about 30° and 120°.

Esters of the formula I can also be obtained by esterifying corresponding carboxylic acids (or reactive derivatives thereof) with alcohols or phenols (or reactive derivatives thereof).

Suitable reactive derivatives of the carboxylic acids mentioned are, in particular, the acid halides, above all the chlorides and bromides, and also the anhydrides, for example also mixed anhydrides, azides or esters, in particular alkyl esters having 1–4 C atoms in the alkyl group.

Suitable reactive derivatives of the alcohols or phenols mentioned are, in particular, the corresponding metal alcoholates or phenolates, respectively, preferably of an alkali metal, such as Na or K.

The esterification is advantageously carried out in the presence of an inert solvent. Solvents which are very suitable are, in particular, ethers, such as diethyl ether, di-n-butyl ether, THF, dioxane or anisole, ketones, such as acetone, butanone or cyclohexanone, amides, such as DMF or phosphoric acid hexamethyltriamide, hydrocarbons, such as benzene, toluene or xylene, halogenated hydrocarbons, such as carbon tetrachloride or tetrachloroethylene, and sulphoxides, such as dimethyl sulphoxide, or sulpholane. Water-immiscible solvents can be used at the same time with advantage for removing by azeotropic distillation the water formed in the course of the esterification. On occasions, an excess of an organic base, for example, pyridine, quinoline or triethylamine, can also be used as a solvent for the esterification. The esterification can also be carried out in the absence of a solvent, for example merely by heating the components in the presence of sodium acetate. The reaction temperature is usually between $-50°$ and $+250°$, preferably between $-20°$ and $+80°$. At these temperatures the esterification reactions are, as a rule, complete after 15 minutes to 48 hours.

In a particular case, the reaction conditions for the esterification depend largely on the nature of the starting materials used. Thus a free carboxylic acid is, as a rule, reacted with a free alcohol or phenol in the presence of a strong acid, for example a mineral acid, such as hydrochloric acid or sulphuric acid. A preferred mode of reaction is to react an acid anhydride or, in particular, an acid chloride with an alcohol, preferably in a basic medium, bases of importance being, in particular, alkali metal hydroxides, such as sodium hydroxide or potassium hydroxide, alkali metal carbonates or bicarbonates, such as sodium carbonate, sodium bicarbonates, potassium carbonate or potassium bicarbonate, alkali metal acetates, such as sodium acetate or potassium acetate, alkaline earth metal hydroxides, such as calcium hydroxide, or organic bases, such as triethylamine, pyridine, lutidine, collidine or quinoline. A further preferred embodiment of the esterification consists in first converting the alcohol or phenol into the sodium alcoholate or potassium alcoholate or phenolate, respectively, for example by treatment with ethanolic sodium hydroxide or potassium hydroxide solution, isolating this alcoholate or phenolate and suspending it, together with sodium bicarbonate or potassium carbonate, with stirring, in acetone or diethyl ether, and adding a solution of the acid chloride or anhydride in diethyl ether, acetone or DMF to this suspension, preferably at temperatures between about $-25°$ and $+20°$.

Nitriles of the formula I (wherein $R^1$ and/or $R^2$ are CN and/or wherein $A^2$, $A^3$ and/or $A^4$ are substituted by at least one CN group) can be prepared by dehydrating corresponding acid amides, for example those in which there is a $CONH_2$ group instead of the radical X. The amides are obtainable, for example, from corresponding esters or acid halides by reacting these with ammonia. Examples of suitable dehydrating agents are inorganic acid chlorides, such as $SOCl_2$, $PCl_3$, $PCl_5$, $POCl_3$, $SO_2Cl_2$, $COCl_2$ and also $P_2O_5$, $P_2S_5$, $AlCl_3$ (for example as the double compound with NaCl), aromatic sulphonic acids and sulphonyl halides. This reaction can be carried out in the presence or absence of an inert solvent at temperatures between about $0°$ C. and $150°$; examples of suitable solvents are bases, such as pyridine or triethylamine, aromatic hydrocarbons, such as benzene, toluene or xylene, or amides, such as DMF.

The abovementioned nitriles of the formula I can also be prepared by reacting corresponding acid halides, preferably the chlorides, with sulphamide, preferably in an inert solvent, such as tetramethylene sulphone at temperatures between about $80°$ and $150°$, preferably at $120°$. The nitriles can be isolated without further treatment after customary working up.

Ethers of the formula I (wherein $R^1$ and/or $R^2$ and/or $R^3$ are an alkoxy group and/or wherein $Z^1$ and/or $Z^2$ are an $-OCH_2-$ or a $-CH_2O-$ group) are obtainable by etherifying corresponding hydroxy compounds, preferably corresponding phenols, the hydroxy compound being preferably first converted into a corresponding metal derivative, for example by treatment with NaH, $NaNH_2$, NaOH, KOH, $Na_2CO_3$ or $K_2CO_3$ into the corresponding alkali metal alcoholate or alkali metal phenolate. This alcoholate or phenolate can then be reacted with the corresponding alkyl halide or sulphonate or dialkyl sulphate, preferably in an inert solvent, such as acetone, 1,2-dimethoxyethane, DMF or dimethyl sulphoxide, or an excess of aqueous or aqueous alcoholic NaOH or KOH at temperatures between about $20°$ and $100°$.

Nitriles of the formula I (wherein $R^1$ and/or $R^2$ are CN and/or wherein $A^2$, $A^3$ and/or $A^4$ are substituted by at least one CN group) can also be prepared by reacting corresponding chlorine or bromine compounds of the formula I (wherein $R^1$ and/or $R^2$ are Cl or Br and/or wherein A is substituted by at least one Cl or Br atom) with a cyanide, preferably with a metal cyanide, such as NaCN, KCN or $Cu_2(CN)_2$, for example in the presence of pyridine in an inert solvent, such as DMF or N-methylpyrrolidone, at temperatures between $20°$ and $200°$.

Compounds of the formula I wherein $R^1$ and/or $R^2$ and/or $R^3$ are F, Cl, Br or CN can also be obtained from the corresponding diazonium salts by replacing the diazonium group by a fluorine, chlorine or bromine atom or by a CN group, for example by the Schiemann or Sandmeyer methods.

The diazonium salts can be prepared, for example, by nitrating compounds corresponding to the formula I but containing one (or two) hydrogen atom(s) instead of the radicals $R^1$ and/or $R^2$ and/or $R^3$, reducing the products to give the corresponding amines and diazotizing the latter, for example with $NaNO_2$ or $KNO_2$ in aqueous solution at temperatures between about $-10°$ and $+10°$.

The diazonium group can be replaced by fluorine by carrying out the diazotization in anhydrous hydrofluoric acid and subsequently heating the product, or by reaction with tetrafluoboric acid to give the diazonium tetrafluoborates, which are then decomposed by means of heat.

Replacement by Cl, Br, or CN is preferably effected by reacting the aqueous diazonium salt solution with $Cu_2Cl_2$, $Cu_2Br_2$ or $Cu_2(CN)_2$ by the Sandmeyer method.

A base of the formula I can be converted into the appropriate acid addition salt by means of an acid. For this reaction it is possible to use inorganic acids, for example sulphuric acid, nitric acid, hydrogen halide acids, such as hydrochloric acid or hydrobromic acid, phosphoric acids, such as orthophosphoric acid, or sulphamic acid, and also organic acids, in particular aliphatic, alicyclic, araliphatic, aromatic or heterocyclic monobasic or polybasic carboxylic, sulphonic or sulphuric acids, for example formic acid, acetic acid, propionic acid, pivalic acid, diethylacetic acid, malonic acid, succinic acid, pimelic acid, fumaric acid, maleic acid, lactic acid, tartaric acid, malic acid, benzoic acid, salicylic acid, 2-phenylpropionic or 3-phenylpropionic acid, citric acid, gluconic acid, ascorbic acid, nicotinic acid, isonicotinic acid, methanesulphonic or ethanesulphonic acid, ethanedisulphonic acid, 2-hydroxyethanesulphonic acid, benzenesulphonic acid, p-toluenesulphonic acid, naphthalenemonosulphonic acid naphthalenedisulphonic acids and laurylsulphuric acid.

Conversely, it is possible to liberate the base of the formula from an acid addition salt of a compound of the formula I by treatment with a base, for example with a strong inorganic base, such as KOH or NaOH. Thus, the salts of this invention are always useful to prepare the corresponding bases of this invention.

The liquid-crystal phases according to the invention comprise of 2 to 25, preferably 3 to 15, components, including at least one compound of the formula I. The other constituents are preferably selected from the nematic or nematogenic substances, in particular the known substances, belonging to the classes of azoxybenzenes, benzylideneanilines, biphenyls, terphenyls, phenyl- or cyclohexylbenzoates, phenyl or cyclohexyl cyclohexanecarboxylates, phenylcyclohexanes, cyclohexylbiphenyls, cyclohexylcyclohexanes, cyclohexylnaphthalenes, 1,4-bis-cyclohexylbenzenes, 4,4'-bis-cyclohexylbiphenyls, phenylpyrimidines, cyclohexylpyrimidines, phenyldioxanes, cyclohexyldioxanes, phenyldithianes, cyclohexyldithianes, 1,2-bis-phenylethanes, 1,2-bis-cyclohexylethanes, 1-phenyl-2-cyclohexylethanes, optionally halogenated stilbenes, benzyl phenyl ether, tolanes and substituted cinnamic acids.

The most important compounds which are suitable for use as constituents of liquid-crystal phases of this type can be characterized by the formula II

R'—L—G—E—R''     II wherein L and E are each a carbocyclic or heterocyclic ring system consisting of the group composed of 1,4-disubstituted benzene and cyclohexane rings, 4,4'-disubstituted biphenyl, phenylcyclohexane and cyclohexylcyclohexane systems, 2,5-disubstituted pyrimidine rings and 1,3-dioxane rings, 2,6-disubstituted naphthalene, dihydronaphthalene, tetrahydronaphthalene, quinazoline and tetrahydroquinazoline, G is

| | |
|---|---|
| —CH=CH— | —N(O)=N— |
| —CH=CX— | —CH=N(O)— |
| —C≡C— | —CH$_2$—CH$_2$— |
| —CO—O— | —CH$_2$—O— |
| —CO—S— | —CH$_2$—S— |
| —CH=N— | —COO—Phe—COO— | or a C—C single bond, X is halogen, preferably chlorine, or —CN, and R' and R'' are alkyl, alkoxy, alkanoyloxy or alkoxycarbonyloxy having up to 18, preferably up to 8, carbon atoms, or one of these radicals can also be CN, NC, NO$_2$, CF$_3$, F, Cl or Br.

In most of these compounds R' and R'' are different from one another, one of these radicals being in most cases an alkyl or alkoxy group. Other variants of the substituents envisaged are also customary, however. Many substances of this type or mixtures thereof are commercially available. All these substances can be prepared by methods known from the literature. The liquid-crystal phases according to the invention contain about 0.1 to 99%, preferably 10 to 95%, of one or more compounds of the formula I. Liquid-crystal phases which are also preferred are those containing 0.1–50%, in particular 0.5–30%, of one or more compounds of the formula I. Isotropic compounds of the formula I can also be used in the phases according to the invention.

The preparation of the liquid-crystal phases according to the invention is effected in a manner which is in itself customary. As a rule, the components are dissolved in one another, preferably at an elevated temperature.

By means of suitable additives it is possible to modify the liquid-crystal phases according to the invention in such a way that they can be used in all types of liquid-crystal display elements hitherto disclosed.

Additives of this type are known to those skilled in the art and are described in detail in the literature. For example, it is possible to add conductive salts, preferably ethyldimethyldodecylammonium 4-hexyloxybenzoate, tetrabutylammonium tetraphenylboranate or complex salts of crown ethers (cf., for example, I. Haller et al., Mol. Cryst. Liq. Cryst. volume 24, pages 249–258 (1973)) in order to improve the conductivity, dichroic dyestuffs in order to prepare colored guest-host systems or substances for modifying the dielectric anisotropy, the viscosity and/or the orientation of the nematic phases. Substances of this type are described, for example, in German Offenlegungsschriften Nos. 2,209,127, 2,240,864, 2,321,632, 2,338,281, 2,450,088, 2,637,430, 2,853,728 and 2,902,177.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the preceding text and the following examples, all temperatures are set forth uncorrected in degrees Celsius and all parts and percentages are by weight; unless otherwise indicated.

EXAMPLES

Example 1

12.2 g of phenylboronic acid and 16.0 g of 2-hydroxymethyloctan-1-ol in 300 ml of toluene are heated at reflux temperature for 6 hours under a water separator. The mixture is allowed to cool and the product is crystallized from alcohol, whereupon 2-phenyl-5-hexyl-1,3,2-dioxaborinane is obtained; clear point (extrapolated): −90° C.

The compounds designated in groups I, II, VIII, IX, XIII and XIV are obtained analogously.

2-(4-Methoxyphenyl)-5-(4-pentylcyclohexyl)-1,3,2-dioxaborinane; phase transitions: (crystalline) 101°, (smectic A) 151.8° and (nematic) 167.2° (isotropic).

2-(4-Propylphenyl)-5-pentyl-1,3,2-dioxaborinane; (crystalline) 46.2° (isotropic); clear point: −70° (extrapolated)

2-(4-Methoxyphenyl)-5-pentyl-1,3,2-dioxaborinane; (crystalline) 58.8° (isotropic); clear point: −40° (extrapolated)

2-(4-Methoxyphenyl)-5-(4-propylcyclohexyl)-1,3,2-dioxaborinane; (crystalline) 127.5°, (smectic A) 140°, (nematic) 162.4° (isotropic)

Example 2

29.6 g of (4-propylcyclohexyl)-dibromoborane (obtained from 4-propylcyclohex-1-ene by means of tribromoborane) are dissolved in 450 ml of pyridine, and 20.6 g of 2-mercaptomethyl-1-mercaptononane are added at such a rate that the temperature of the reaction mixture does not rise above 40°. When the addition is complete, the mixture is stirred for a further 6 hours at 20° C. and is poured into 2 l of ice water. The precipitated crystals are filtered off with suction, washed with water and dried. This gives 2-(4-propylcyclohexyl)-5-heptyl-1,3,2-dithiaborinane.

The compounds designated in groups III–VII and X–XII are obtained analogously.

Example 3

37.9 g of 2-(4'-(4-pentylcyclohexyl)-biphenyl-4-yl)-3-aminopropan-1-ol (obtainable from 4-(4-pentylcyclohexyl)-biphenyl by chloromethylation and reacting the product with sodium cyanide, subjecting the resulting 4-cyanomethyl-4'-(4-pentylcyclohexyl)-biphenyl to a condensation reaction with diethyl carbonate to give 2-(4'-(4-pentylcyclohexyl)-biphenyl-4'-yl)-malonic acid nitrile-ester and reducing the latter with lithium aluminium hydride) and 25 g of triethylamine are dissolved in 500 ml of methylene dichloride, and 12.5 g of dichloropropylborane are added slowly, in the course of which the reaction mixture comes to the boil. When the addition is complete, the mixture is heated at reflux temperature for a further 4 hours, allowed to cool and washed with water. After being dried, the organic phase is freed from the solvent. Crystallizing the residue gives 2-propyl-5-(4'-(4-pentylcyclohexyl)biphenyl-4-yl)-1,3,2-oxazaborinane.

The compounds mentioned in group XV are obtained analogously.

Example 4

20 g of dimethoxy-(2-propylpyrimidin-5-yl)-borane (obtained from 2-propylpyrimidin-5-ylmagnesium chloride and trimethoxyborane) and 30 g of 2-hydroxymethylnonan-1-ol are heated at 100° for 12 hours, the methanol formed being removed continuously by distillation. When the reaction is complete, excess nonanol is removed under reduced pressure, and 2-(2-propylpyrimidin-5-yl)-5-heptyl-1,3,2-dioxaborinane is obtained.

The compounds designated in groups XVI and XVII are obtained analogously.

Example 5

17.2 g of 2-hydroxy-5-pentyl-1,3,2-dioxaborinane (prepared from trichloroborane and 2-hydroxymethylheptan-1-ol, followed by hydrolysis), 16.6 g of 4-cyanobenzoyl chloride and 15 ml of pyridine in 500 ml of toluene are heated at reflux temperature for 4 hours. Water is added to the mixture, the phases are separated, the organic phase is washed with water, dried over sodium sulphate and evaporated, and (5-pentyl-1,3,2-dioxaborinan-2-yl) 4-cyanobenzoate is obtained.

The compounds designated in groups XVIII–XXI are obtained analogously.

Example 6

27.6 g of 2-(4-carboxyphenyl)-5-pentyl-1,3,2-dioxaborinane (prepared from dihydroxy-(4-carboxyphenyl)-borane and 2-hydroxymethylheptan-1-ol analogously to Example 1) are converted into the acid chloride by heating with 12 g of thionyl chloride. The mixture is evaporated, the residue is dissolved in 300 ml of toluene, 15 ml of pyridine and 15.2 g of 4-propoxyphenol are added, and the mixture is boiled for 5 hours. After being washed with water, the organic phase is dried and concentrated to give the residue.

This gives 4-propoxyphenyl 4-(5-pentyl-1,3,2-dioxaborinan-2-yl)-benzoate.

The compounds indicated in groups XXII–XXIV and XXVI–XXVIII are obtained analogously.

Example 7

23 g of 1-(4'-propylbiphenyl-4-yl)-2-bromoethane in 100 ml of diethyl ether are converted into the Grignard compound by means of 3 g of magnesium turnings. The ethereal solution of the organomagnesium compound is added dropwise, at −60°, to 20 g of 2-methoxy-5-hexyl-1,3,2-dioxaborinane (prepared from trimethoxyborane and 2-hydroxymethyloctan-1-ol analogously to Example 4) in 200 ml of ether. When the addition is complete, the mixture is stirred for a further 5 hours at −40° and is then allowed to warm up to 20° C. Water is added, and the organic phase is separated off and freed from solvent. This gives 1-(4'-propylbiphenyl-4-yl)-2-(5-hexyl-1,3,2-dioxaborinan-2-yl)-ethane.

The compounds indicated in groups XXX–XXXII and XXXIV are obtained analogously.

Example 8

32.4 g of 2-iodomethyl-5-heptyl-1,3,2-dioxaborinane (prepared from dibromoiodomethylborane (Matteson, Cheng; J. org. Chem. 33 (1968) 3055) and 2-hydroxymethylnonan-1-ol analogously to Example 2) are added to the suspension of the corresponding sodium phenolate obtained from 2.5 g of sodium hydride and 21.4 g of 2propyl-5(4-hydroxyphenyl)-pyrimidine in 250 ml of dimethylformamide. The mixture is then stirred for 10 hours at 40° and is then poured into 2 l of water. 2-(4-(2Propylpyrimidin-2-yl)phenoxymethyl)-5-heptyl-1,3,2-dioxaborinane is obtained by filtering off the precipitated crystals with suction, washing them with water and drying.

The compounds indicated in group XXXIII are obtained analogously.

The following examples relate to mixtures according to the invention:

Example A

A mixture of:
25% of 2-(4-propoxyphenyl)-5-pentyl-1,3,2-dioxaborinane,
15% of trans-4-(4propylcyclohexyl)-benzonitrile,
25% of trans-4-(4-pentylcyclohexyl)-benzonitrile,
13% of trans-4-(4-ethoxyphenyl)-propylcyclohexane,
12% of trans-4-(4-hexyloxyphenyl)-propylcyclohexane and
10% of 4(trans-4-pentylcyclohexyl)-4'-(trans-4-propylcyclohexyl)-biphenyl
is prepared.

Example B

A mixture of:
20% of 2-(4-cyanophenyl)-5-hexyl-1,3,2-dithiaborinane,
15% of 2-(4-ethylphenyl)-5-propyl-1,3-dioxane,
12% of 2-(4-butoxyphenyl)-5-propyl-1,3-dioxane,
14% of trans-4-(4-hexylphenyl)-ethylcyclohexane,
17% of 4-butyl-4'-cyanobiphenyl,
15% of trans-4-(4-(4-pentylcyclohexyl)-cyclohexyl)-benzonitrile and
7% of trans-4-(4-(4-pentylcyclohexyl)-cyclohexyl)-cyanocyclohexane
is prepared.

Example C

A mixture of:
30% of trans-2-(4-cyanocyclohexyl)-5-heptyl-1,3,2-dioxaborinane,
25% of trans-2-(4-cyanocyclohexyl)-5-heptyl-1,3,2-diazaborinane,
14% of 4-ethoxyphenyl trans-4-propylcyclohexanecarboxylate
14% of 4-propylcyclohexyl trans-4-butylcyclohexanecarboxylate.
10% of 4-(4-propylcyclohexyl)-phenyl trans-4-butylcyclohexanecarboxylate and
7% of 4-(5-heptyl-1,3-dioxan-2-yl)-benzonitrile
is prepared.

Example D

A mixture of:
30% of 4-propylphenyl 4-(5-pentyl-1,3,2-thioxaborinan-2-yl)-benzoate,
20% of trans-2-(4-cyanocyclohexyl)-5-butyl-1,3-dioxane,
20% of trans-2-(4-butanoyloxycyclohexyl)-5-butyl-1,3-dioxane,
15% of trans-2-(4-hexylcyclohexyl)-2-fluorobenzonitrile and
15% of 4-(4-ethylphenoxycarbonyl)-phenyl 4-heptylbenzoate
is prepared.

Example E

A mixture of:
25% of 4-propylcyclohexyl trans-4-(5-pentyl-1,3,2-dioxaborinane-2-yl)-cyclohexanecarboxylate,
18% of 4-propylcyclohexyl trans-4-(5-pentyl-1,3,2-dithiaborinan-2-yl)-cyclohexanecarboxylate,
15% of 4-propylcyclohexyl trans-4-(4-pentylcyclohexyl)cyclohexanecarboxylate,
15% of 4-cyanophenyl trans-4-heptylcyclohexanecarboxylate,
14% of 4-cyanophenyl 4-butoxybenzoate and
13% of 4-(4-hexyloxycyclohexyl)-cyanocyclohexane is prepared.

Example F

A mixture of:
27% of 4-cyanophenyl 4-(5-pentyl-1,3,2-dioxaborinan-2-yl)-benzoate,
27% of 4-cyanophenyl 4-(5-propyl-1,3,2-dioxaborinan-2-yl)-benzoate,
15% of 4-pentylphenyl 4-methoxybenzoate,
15% of 4-propylphenyl 4-(4-pentylcyclohexyl)-benzoate,
10% of 4-fluorophenyl 4-(4-butylcyclohexyl)-benzoate and
6% of 1-(4(4-butylcyclohexyl)-cyclohexyl)-2-(4-hexylcyclohexyl)-ethane
is prepared.

Example G

A mixture of:
38% of trans-4-(4-cyanophenyl)-pentylcyclohexane
15% of 2-(4-cyanophenyl)-5-propyl-1,3,2-dioxaborinane,
15% of 2-(4-cyanophenyl)-5-pentyl-1,3,2-dioxaborinane,
20% of 2(4-cyanophenyl)-5-hexyl-1,3,2-dioxaborinane and
12% of trans-4-(4-cyanobiphenyl-4'-yl)-pentylcyclohexane
is prepared.

Example H

A mixture of
35% of 2-(4-butoxyphenyl)-5-pentyl-2,5-dihydrodiazaborine,
24% of 4-methoxy-4'-(4-heptylcyclohexyl)-biphenyl,
20% of 1-(4-propylcyclohexyl)-2(2'-fluoro-4'-pentylbiphenyl-4-yl)-ethane,
16% of 4-hexylphenyl 1-cyano-4-ethylcyclohexanecarboxylate and
5% of 2,3-dicyano-4-pentylphenyl 4-propylcyclohexanecarboxylate
is prepared.

Example I

A mixture of:
20% of 2-(4-cyanophenyl)-5-butyl-1,3,2-dithiaborinane,
20% of 4-pentylphenyl 4-(5-propyl-1,3,2-dioxaborinan-2-yl)-benzoate,
18% of 4-pentylphenyl trans-4-propylcyclohexanecarboxylate,
17% of 2-(4-pentylcyclohexyl)-5-ethyl-1,3,2-dioxaborinane,
15% of 4-heptylphenyl 4-(5-propyl-1,3,2-dioxaborinan-2-yl)-benzoate and
10% of 4'-heptyl-4-cyanobiphenyl
is prepared.

Example J

A mixture of:
35% of 2-(4-propylcyclohexyl)-5-pentyl-1,3,2-thioxaborinane,
25% of 4-(4-propylcyclohexyl)-pentylcyclohexane,
15% of 2-(4-cyanophenyl)-5-(4-ethylphenyl)-pyrimidine,
10% of 1-(4-pentylcyclohexyl)-2-(4-propylcyclohexyl)-ethane,
9% of 4-propylcyclohexyl 1-cyano-4-pentylcyclohexane-1-carboxylate and
6% of 2-fluoro-4-(4-heptylcyclohexyl)-4'-(4-pentylcyclohexyl)-biphenyl
is prepared.

Example K

A mixture of:
36% of 2-(4-heptylcyclohexyl)-5-propyl-1,3,2-dioxaborinane,
22% of 4-heptyl-4'-(4-ethylcyclohexyl)-biphenyl,
15% of 2-(4-butoxyphenyl)-5-(4-ethoxycyclohexyl)-pyrimidine,
15% of 4-(4-pentanoyloxycyclohexyl)-propylcyclohexane, 7% of 1-cyano-1-(4-butylcyclohexyl)-4-(4-ethylcyclohexyl)-cyclohexane and
5% of 1-(4-propylcyclohexyl)-2-(4-(4-cyanophenyl)-cyclohexyl)-ethane
is prepared.

Example L

A mixture of:
28% of 2-(4-propoxycyclohexyl)-5-pentyl-1,3,2-dioxaborinane,
28% of 2-(4-propoxycyclohexyl)-5-pentyl-1,3,2-dithiaborinane,
20% of 4-(4-propoxycyclohexyl)-5-pentylcyclohexane,
10% of 2-(4-cyanophenyl)-5-(4-butylcyclohexyl)-pyrimidine,
8% of 4-cyano-4'-(4-propylcyclohexyl)-biphenyl and
6% of 4-(4-(3-fluoro-4-cyanophenyl)-cyclohexyl)-butylcyclohexane
is prepared.

Example M

A mixture of:
30% of 2-(4-hexyloxyphenyl)-5-pentyl-1,3,2-dioxaborinane,
25% of 2-(4-butoxyphenyl)-5-pentylpyrimidine,
23% of 2-(4-propylcyclohexyl)-5-heptyl-1,3-dioxane,
17% of 4-cyanophenyl 4-(4-hexylcyclohexyl)-benzoate and
5% of 1-cyano-1-(4-butylcyclohexyl)-2-(4-hexylcyclohexyl)ethane
is prepared.

Example N

A mixture of:
24% of 4-cyanocyclohexyl 4-(5-heptyl-1,3,2-dioxaborinan-2-yl)-cyclohexanecarboxylate,
21% of 4-cyanocyclohexyl 4-(5-pentyl-1,3,2-dioxaborinan-2-yl)-cyclohexanecarboxylate,
18% of 2-(4-propoxycyclohexyl)-5-pentyl-1,3-dioxane,
15% of 2-(4-cyanophenyl)-5-hexylpyrimidine,
12% of 4-(4-propoxycyclohexyl)-cyclohexyl)-heptylcyclohexane
5% of 3-fluoro-4-cyanophenyl 4-butylbenzoate and
5% of 1-(4-butylcyclohexyl)-2-(4-(4-hexylcyclohexyl)-biphenyl-4'-yl)-ethane.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. In a liquid crystalline phase comprising at least two components, the improvement wherein at least one component is a heterocyclic boron compound of the formula
   $R^1$—$A^1$—$Z^1$—$A^2$—$R^2$—
   wherein
   $R^1$ and $R^2$ are independently alkyl of 1–15C atoms, alkyl of 1–15C atoms wherein one or two non-adjacent CH$_2$ groups are replaced by —O—, —CO—, —O—CO—, —CO—O— or —CH=CH—, or $R^2$ is H, F, Cl, Br, NCS, CN or $R^3$—$A^3$—$Z^2$,
   $A^1$ is

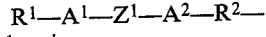

A is

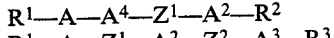

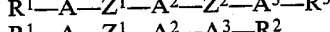

the Zs are identical or different and are —NH—CH$_2$—, —O—CH$_2$— or —S—CH$_2$, each of which is not linked to boron via a carbon atom,
M and N are each independently —CH$_2$—, —CO—, —CH$_2$CH$_2$—, —CH$_2$O— or —OCH$_2$—,
$A^2$, $A^3$ and $A^4$ are each independently 1,4-cyclohexylene; 1,4-phenylene; pyridine- or pyrimidine-2,5-diyl;
$Z^1$ and $Z^2$ are each independently —CO—O—, —O—CO—, —CH$_2$CH$_2$—, —OCH$_2$—, —CH$_2$—O—, or a single bond, and
$R^3$ is alkyl of 1–15C atoms, alkyl of 1–15C atoms wherein one or two non-adjacent CH$_2$ groups are replaced by —O—, —CO—, —O—CO—, —CO—O— or —CH=CH— or is H, F, Cl, Br, NCS or CN.

2. A phase of claim 1, wherein said compound is of the formula
   $R^1$—A—$Z^1$—$A^2$—$R^2$
   or
   $R^1$—A—$A^2$—$R^2$.

3. A phase of claim 1, wherein said compound is of the formula
   $R^1$—A—$A^4$—$Z^1$—$A^2$—$R^2$
   $R^1$—A—$Z^1$—$A^2$—$Z^2$—$A^3$—$R^3$
   $R^1$—A—$Z^1$—$A^2$—$A^3$—$R^2$
   $R^1$—A—$A^2$—$Z^2$—$A^3$—$R^3$
   or
   $R^1$—A—$A^4$—$A^2$—$R^2$.

4. A phase of claim 1, wherein said compound is of the formula
   $R^1$—A—$A^4$—$Z^1$—$A^2$—$Z^2$—$A^3$—$R^3$
   $R^1$—A—$A^4$—$A^2$—$A^3$—$R^3$
   $R^1$—A—$A^4$—$A^2$—$Z^2$—$A^3$—$R^3$,
   or
   $R^1$—A—$A^4$—$Z^1$—$A^2$—$A^3$—$R^3$.

5. A phase of claim 1, wherein $R^1$, $R^2$ and $R^3$ are alkyl or alkoxy.

6. A phase of claim 1, wherein $A^2$, $A^3$ and $A^4$ are Cy, Phe, Pyr, OBO, OBS, OBN, OBNH, SBS, SBN, SBNH, NBN, NBNH, or NHBNH, wherein Cy or Cyc is a 1,4-cyclohexylene group, OBO is a 1,3,2-dioxaborinane-2,5-diyl group, OBS is a 1,3,2-oxathiaborinane-2,5-diyl group, OBN is a 2,5-dihydro-6H-1,3,2-oxazaborine-2,5-diyl group, OBNH is a 1,3,2-oxazaborinane-2,5-diyl group, SBS is a 1,3,2-dithiaborinane-2,5-diyl group, SBN is a 2,5-dihydro-6H-1,3,2-thiazaborine-2,5-diyl group, SBNH is a 1,3,2-thiazaborinane-2,5-diyl group, NBN is a 2,5-dihydro-6H-1,3,2-diazaborine-2,5-diyl group, NBNH is a 2,3,4,5-tetrahydro-6H-1,3,2-diazaborine-2,5-diyl group, NHBNH is a 1,3,2-diazaborinane- 2,5-diyl group, Phe is a 1,4-phenylene group, and Pyr is a pyrimidine-2,5-diyl group.

7. A phase of claim 6, wherein said compound is of the formula

R$^1$—OBO—COO—Phe—R$^2$
R$^1$—OBO—CH$_2$CH$_2$—Phe—R$^2$
R$^1$—OBO—Phe—COO—Phe—R$^2$
R$^1$—OBO—Phe—CH$_2$CH$_2$—Phe—R$^2$
R$^1$—OBO—Phe—CH$_2$CH$_2$—Cy—R$^2$
R$^1$—OBO—Phe—CH$_2$CH$_2$—Phe—Cy—R$^3$
R$^1$—OBO—Phe—R$^2$
R$^1$—OBO—Phe—Phe—R$^2$
R$^1$—OBO—Phe—Phe—Cy—R$^3$
R$^1$—OBO—Cy—Phe—R$^2$
R$^1$—Cy—OBO—Phe—R$^2$
R$^1$—OBO—Cy—R$^2$
R$^1$—OBO—Cy—Cy—R$^3$
R$^1$—OBO—Pyr—R$^2$
R$^1$—OBO—CH$_2$CH$_2$—Phe—Phe—R$^3$
R$^1$—OBO—CH$_2$CH$_2$—Phe—Cy—R$^3$
R$^1$—OBS—COO—Phe—R$^2$
R$^1$—OBS—CH$_2$CH$_2$—Phe—R$^2$
R$^1$—OBS—Phe—COO—Phe—R$^2$
R$^1$—OBS—Phe—CH$_2$CH$_2$—Phe—R$^2$
R$^1$—OBS—Phe—CH$_2$CH$_2$—Cy—R$^2$
R$^1$—OBS—Phe—CH$_2$CH$_2$—Phe—Cy—R$^3$
R$^1$—OBS—Phe—R$^2$
R$^1$—OBS—Phe—Phe—R$^2$
R$^1$—OBS—Phe—Phe—Cy—R$^3$
R$^1$—OBS—Cy—Phe—R$^2$
R$^1$—Cy—OBS—Phe—R$^2$
R$^1$—OBS—Cy—R$^2$
R$^1$—OBS—Cy—Cy—R$^3$
R$^1$—OBS—Pyr—R$^2$
R$^1$—OBS—CH$_2$CH$_2$—Phe—Phe—R$^3$
R$^1$—OBS—CH$_2$CH$_2$—Phe—Cy'R$^3$
R$^1$—OBN—COO—Phe—R$^2$
R$^1$—OBN—CH$_2$CH$_2$—Phe—R$^2$
R$^1$—OBN—Phe—COO—Phe—R$^2$
R$^1$—OBN—Phe—CH$_2$CH$_2$—Phe—R$^2$
R$^1$—OBN—Phe—CH$_2$CH$_2$—Cy—R$^2$
R$^1$—OBN—Phe—CH$_2$CH$_2$—Phe—Cy—R$^3$
R$^1$—OBN—Phe—R$^2$
R$^1$—OBN—Phe—Phe—R$^2$
R$^1$—OBN—Phe—Phe—Cy—R$^3$
R$^1$—OBN—Cy—Phe—R$^2$
R$^1$—Cy—OBN—Phe—R$^2$
R$^1$—OBN—Cy—R$^2$
R$^1$—OBN—Cy—Cy—R$^3$
R$^1$—OBN—Pyr—R$^2$
R$^1$—OBN—CH$_2$CH$_2$—Phe—Phe—R$^3$
R$^1$—OBN—CH$_2$CH$_2$—Phe—Cy—R$^3$
R$^1$—OBNH—COO—Phe—R$^2$
R$^1$—OBNH—CH$_2$CH$_2$—Phe—R$^2$
R$^1$—OBNH—Phe—COO—Phe—R$^2$
R$^1$—OBNH—Phe—CH$_2$CH$_2$—Phe—R$^2$
R$^1$—OBNH—Phe—CH$_2$CH$_2$—Cy—R$^2$
R$^1$—OBNH—Phe—CH$_2$CH$_2$—Phe—Cy—R$^3$
R$^1$—OBNH—Phe—R$^2$
R$^1$—OBNH—Phe—Phe—R$^2$
R$^1$—OBNH—Phe—Phe—Cy—R$^3$
R$^1$—OBNH—Cy—Phe—R$^2$
R$^1$—Cy—OBNH—Phe—R$^2$
R$^1$—OBNH—Cy—R$^2$
R$^1$—OBNH—Cy—Cy—R$^3$
R$^1$—OBNH—Pyr—R$^2$
R$^1$—OBNH—CH$_2$CH$_2$—Phe—Phe—R$^3$
R$^1$—OBNH—CH$_2$CH$_2$—Phe—Cy—R$^3$
R$^1$—SBS—COO—Phe—R$^2$
R$^1$—SBS—CH$_2$CH$_2$—Phe—R$^2$
R$^1$—SBS—Phe—COO—Phe—R$^2$
R$^1$—SBS—Phe—CH$_2$CH$_2$—Phe—R$^2$
R$^1$—SBS—Phe—CH$_2$CH$_2$—Cy—R$^2$
R$^1$—SBS—Phe—CH$_2$CH$_2$—Phe—Cy—R$^3$
R$^1$—SBS—Phe—R$^2$
R$^1$—SBS—Phe—Phe—R$^2$
R$^1$—SBS—Phe—Phe—Cy—R$^3$
R$^1$—SBS—Cy—Phe—R$^2$
R$^1$—Cy—SBS—Phe—R$^2$
R$^1$—SBS—Cy—R$^2$
R$^1$—SBS—Cy—Cy—R$^3$
R$^1$—SBS—Pyr—R$^2$
R$^1$—SBS—CH$_2$CH$_2$—Phe—Phe—R$^3$
R$^1$—SBS—CH$_2$CH$_2$—Phe—Cy—R$^3$
R$^1$—SBN—COO—Phe—R$^2$
R$^1$—SBN—CH$_2$CH$_2$—Phe—R$^2$
R$^1$—SBN—Phe—COO—Phe—R$^2$
R$^1$—SBN—Phe—CH$_2$CH$_2$—Phe—R$^2$
R$^1$—SBN—Phe—CH$_2$CH$_2$—Cy—R$^2$
R$^1$—SBN—Phe—CH$_2$CH$_2$—Phe—Cy—R$^3$
R$^1$—SBN—Phe—R$^2$
R$^1$—SBN—Phe—Phe—R$^2$
R$^1$—SBN—Phe—Phe—Cy—R$^3$
R$^1$—SBN—Cy—Phe—R$^2$
R$^1$—Cy—SBN—Phe—R$^2$
R$^1$—SBN—Cy—R$^2$
R$^1$—SBN—Cy—Cy—R$^3$
R$^1$—SBN—Pyr—R$^2$
R$^1$—SBN—CH$_2$CH$_2$—Phe—Phe—R$^3$
R$^1$—SBN—CH$_2$CH$_2$—Phe—Cy—R$^3$
R$^1$—SBNH—COO—Phe—R$^2$
R$^1$—SBNH—CH$_2$CH$_2$—Phe—R$^2$
R$^1$—SBNH—Phe—COO—Phe—R$^2$
R$^1$—SBNH—Phe—CH$_2$CH$_2$—Phe—R$^2$
R$^1$—SBNH—Phe—CH$_2$CH$_2$—Cy—R$^2$
R$^1$—SBNH—Phe—CH$_2$CH$_2$—Phe—Cy—R$^3$
R$^1$—SBNH—Phe—R$^2$
R$^1$—SBNH—Phe—Phe—R$^2$
R$^1$—SBNH—Phe—Phe—Cy—R$^3$
R$^1$—SBNH—Cy—Phe—R$^2$
R$^1$—Cy—SBNH—Phe—R$^2$
R$^1$—SBNH—Cy—R$^2$
R$^1$—SBNH—Cy—Cy—R$^3$
R$^1$—SBNH—Pyr—R$^2$
R$^1$—SBNH—CH$_2$CH$_2$—Phe—Phe—R$^3$
R$^1$—SBNH—CH$_2$CH$_2$—Phe—Cy—R$^3$
R$^1$—NBN—COO—Phe—R$^2$
R$^1$—NBN—CH$_2$CH$_2$—Phe—R$^2$
R$^1$—NBN—Phe—COO—Phe—R$^2$
R$^1$—NBN—Phe—CH$_2$CH$_2$—Phe—R$^2$
R$^1$—NBN—Phe—CH$_2$CH$_2$—Cy—R$^2$
R$^1$—NBN—Phe—CH$_2$CH$_2$—Phe—Cy—R$^3$
R$^1$—NBN—Phe—R$^2$
R$^1$—NBN—Phe—Phe—R$^2$
R$^1$—NBN—Phe—Phe—Cy—R$^3$
R$^1$—NBN—Cy—Phe—R$^2$
R$^1$—Cy—NBN—Phe—R$^2$
R$^1$—NBN—Cy—R$^2$
R$^1$—NBN—Cy—Cy—R$^3$
R$^1$—NBN—Pyr—R$^2$
R$^1$—NBN—CH$_2$CH$_2$—Phe—Phe—R$^3$
R$^1$—NBN—CH$_2$CH$_2$—Phe—Cy—R$^3$
R$^1$—NBNH—COO—Phe—R$^2$
R$^1$—NBNH—CH$_2$CH$_2$—Phe—R$^2$
R$^1$—NBNH—Phe—COO—Phe—R$^2$
R$^1$—NBNH—Phe—CH$_2$CH$_2$—Phe—R$^2$
R$^1$—NBNH—Phe—CH$_2$CH$_2$—Cy—R$^2$

R¹—NBNH—Phe—CH₂CH₂—Phe—Cy—R³
R¹—NBNH—Phe—R²
R¹—NBNH—Phe—Phe—R²
R¹—NBNH—Phe—Phe—Cy—R³
R¹—NBNH—Cy—Phe—R²
R¹—Cy—NBNH—Phe—R²
R¹—NBNH—Cy—R²
R¹—NBNH—Cy—Cy—R³
R¹—NBNH—Pyr—R²
R¹—NBNH—CH₂CH₂—Phe—Phe—R³
R¹—NBNH—CH₂CH₂—Phe—Cy—R³
R¹—NHBNH—COO—Phe—R²
R¹—NHBNH—CH₂CH₂—Phe—R²
R¹—NHBNH—Phe—COO—Phe—R²
R¹—NHBNH—Phe—CH₂CH₂—Phe—R²
R¹—NHBNH—Phe—CH₂CH₂—Cy—R²
R¹—NHBNH—Phe—CH₂CH₂—Phe—Cy—R³
R¹—NHBNH—Phe—R²
R¹—NHBNH—Phe—Phe—R²
R¹—NHBNH—Phe—Phe—Cy—R³
R¹—NHBNH—Cy—Phe—R²
R¹—Cy—NHBNH—Phe—R²
R¹—NHBNH—Cy—R²
R¹—NHBNH—Cy—Cy—R³
R¹—NHBNH—Pyr—R²
R¹—NHBNH—CH₂CH₂—Phe—Phe—R³ or

R¹—NHBNH—CH₂CH₂—Phe—Cy—R³.

8. A phase of claim 1, wherein the non-aromatic rings are in the trans-1,4-position.

9. A phase of claim 1, wherein —A— is 1,3,2-dioxaborinane-2,5-diyl, 1,3,2-dithiaborinane-2,5-diyl, 1,3,2-diazaborinane-2,5-diyl, 2,5-dihydro-1,3,2-diazaborine-2,5-diyl, 1,3,2-oxazaborinane-2,5-diyl, 2,5-dihydro-6H-1,3,2-oxazaborine-2,5-diyl, 2,5-dihydro-6H-1,3,2-thiazaborine-2,5-diyl, 2,3,4,5-tetrahydro-1,3,2-diazaborine-2,5-diyl, 1,3,2-thiazaborinane-2,5-diyl or 1,3,2-oxathiaborinane-2,5-diyl.

10. A phase of claim 6 of the formula
Alkyl—A—Phe—CN
Alkyl—A—Phe—Methyl
Alkyl—A—Phe—Ethyl
Alkyl—A—Phe—Propyl
Alkyl—A—Phe—Butyl
Alkyl—A—Phe—Pentyl
Alkyl—A—Phe—Hexyl
Alkyl—A—Phe—Heptyl
Alkyl—A—Phe—Octyl
Alkyl—A—Phe—Nonyl
Alkyl—A—Phe—Decyl
Alkyl—A—Phe—Methoxy
Alkyl—A—Phe—Ethoxy
Alkyl—A—Phe—Propoxy
Alkyl—A—Phe—Butoxy
Alkyl—A—Phe—Pentoxy
Alkyl—A—Phe—Hexyloxy
Alkyl—A—Phe—Heptyloxy
Alkyl—A—Phe—Octyloxy
Alkyl—A—Phe—Nonyloxy
Alkyl—A—Phe—Decyloxy
Alkyl—A—Cyc—CN
Alkyl—A—Cyc—Methyl
Alkyl—A—Cyc—Ethyl
Alkyl—A—Cyc—Propyl
Alkyl—A—Cyc—Butyl
Alkyl—A—Cyc—Pentyl
Alkyl—A—Cyc—Hexyl
Alkyl—A—Cyc—Heptyl
Alkyl—A—Cyc—Octyl
Alkyl—A—Cyc—Nonyl
Alkyl—A—Cyc—Decyl
Alkyl—A—Cyc—Methoxy
Alkyl—A—Cyc—Ethoxy
Alkyl—A—Cyc—Propoxy
Alkyl—A—Cyc—Butoxy
Alkyl—A—Cyc—Pentoxy
Alkyl—A—Cyc—Hexyloxy
Alkyl—A—Cyc—Heptyloxy
Alkyl—A—Cyc—Octyloxy
Alkyl—A—Cyc—Nonyloxy
Alkyl—A—Cyc—Decyloxy
Alkyl—A—Cyc—Methoxycarbonyl
Alkyl—A—Cyc—Ethoxycarbonyl
Alkyl—A—Cyc—Propoxycarbonyl
Alkyl—A—Cyc—Butoxycarbonyl
Alkyl—A—Cyc—Pentoxycarbonyl
Alkyl—A—Cyc—Hexyloxycarbonyl
Alkyl—A—Cyc—Heptyloxycarbonyl
Alkyl—A—Cyc—Octyloxycarbonyl
Alkyl—A—Cyc—Nonyloxycarbonyl
Alkyl—A—Cyc—Decyloxycarbonyl
Alkyl—A—Cyc—Methylcarbonyloxy
Alkyl—A—Cyc—Ethylcarbonyloxy
Alkyl—A—Cyc—Propylcarbonyloxy
Alkyl—A—Cyc—Butylcarbonyloxy
Alkyl—A—Cyc—Pentylcarbonyloxy
Alkyl—A—Cyc—Hexylcarbonyloxy
Alkyl—A—Cyc—Hetpylcarbonyloxy
Alkyl—A—Cyc—Octylcarbonyloxy
Alkyl—A—Cyc—Nonylcarbonyloxy
Alkyl—A—Cyc—Decylcarbonyloxy
Methyl—A—Cyc—Oxaalkyl
Ethyl—A—Cyc—Oxaalkyl
Propyl—A—Cyc—Oxaalkyl
Butyl—A—Cyc—Oxaalkyl
Pentyl—A—Cyc—Oxaalkyl
Hexyl—A—Cyc—Oxaalkyl
Heptyl—A—Cyc—Oxaalkyl
Octyl—A—Cyc—Oxaalkyl
Nonyl—A—Cyc—Oxaalkyl
Decyl—A—Cyc—Oxaalkyl
Alkyl—A—Phe—Phe—CN
Alkyl—A—Phe—Phe—Methyl
Alkyl—A—Phe—Phe—Ethyl
Alkyl—A—Phe—Phe—Propyl
Alkyl—A—Phe—Phe—Butyl
Alkyl—A—Phe—Phe—Pentyl
Alkyl—A—Phe—Phe—Hexyl
Alkyl—A—Phe—Phe—Heptyl
Alkyl—A—Phe—Phe—Octyl
Alkyl—A—Phe—Phe—Nonyl
Alkyl—A—Phe—Phe—Decyl
Alkyl—A—Phe—Phe—Methoxy
Alkyl—A—Phe—Phe—Ethoxy
Alkyl—A—Phe—Phe—Propoxy
Alkyl—A—Phe—Phe—Butoxy
Alkyl—A—Phe—Phe—Pentoxy
Alkyl—A—Phe—Phe—Hexyloxy
Alkyl—A—Phe—Phe—Heptyloxy
Alkyl—A—Phe—Phe—Octyloxy
Alkyl—A—Phe—Phe—Nonyloxy
Alkyl—A—Phe—Phe—Decyloxy
Alkyl—A—Cyc—Phe—CN
Alkyl—A—Cyc—Phe—Methyl
Alkyl—A—Cyc—Phe—Ethyl
Alkyl—A—Cyc—Phe—Propyl
Alkyl—A—Cyc—Phe—Butyl
Alkyl—A—Cyc—Phe—Pentyl
Alkyl—A—Cyc—Phe—Hexyl
Alkyl—A—Cyc—Phe—Heptyl
Alkyl—A—Cyc—Phe—Octyl Alkyl—A—Cyc—Phe—Nonyl
Alkyl—A—Cyc—Phe—Decyl
Alkyl—A—Cyc—Phe—Methoxy
Alkyl—A—Cyc—Phe—Ethoxy
Alkyl—A—Cyc—Phe—Propoxy
Alkyl—A—Cyc—Phe—Butoxy
Alkyl—A—Cyc—Phe—Pentoxy
Alkyl—A—Cyc—Phe—Hexyloxy
Alkyl—A—Cyc—Phe—Heptyloxy
Alkyl—A—Cyc—Phe—Octyloxy
Alkyl—A—Cyc—Phe—Nonyloxy
Alkyl—A—Cyc—Phe—Decyloxy
Alkyl—A—Cyc—Cyc—CN
Alkyl—A—Cyc—Cyc—Methyl
Alkyl—A—Cyc—Cyc—Ethyl
Alkyl—A—Cyc—Cyc—Propyl
Alkyl—A—Cyc—Cyc—Butyl
Alkyl—A—Cyc—Cyc—Pentyl
Alkyl—A—Cyc—Cyc—Hexyl
Alkyl—A—Cyc—Cyc—Heptyl
Alkyl—A—Cyc—Cyc—Octyl
Alkyl—A—Cyc—Cyc—Nonyl
Alkyl—A—Cyc—Cyc—Decyl
Alkyl—Cyc—A—Phe—CN
Alkyl—Cyc—A—Phe—Methyl
Alkyl—Cyc—A—Phe—Ethyl
Alkyl—Cyc—A—Phe—Propyl
Alkyl—Cyc—A—Phe—Butyl
Alkyl—Cyc—A—Phe—Pentyl
Alkyl—Cyc—A—Phe—Hexyl
Alkyl—Cyc—A—Phe—Heptyl
Alkyl—Cyc—A—Phe—Octyl
Alkyl—Cyc—A—Phe—Nonyl
Alkyl—Cyc—A—Phe—Decyl
Alkyl—Cyc—A—Phe—Methoxy
Alkyl—Cyc—A—Phe—Ethoxy
Alkyl—Cyc—A—Phe—Propoxy
Alkyl—Cyc—A—Phe—Butoxy
Alkyl—Cyc—A—Phe—Pentoxy
Alkyl—Cyc—A—Phe—Hexyloxy
Alkyl—Cyc—A—Phe—Heptyloxy
Alkyl—Cyc—A—Phe—Octyloxy
Alkyl—Cyc—A—Phe—Nonyloxy
Alkyl—Cyc—A—Phe—Decyloxy
Cyan—Cyc—Phe—Phe—A—Alkyl
Methyl—Cyc—Phe—Phe—A—Alkyl
Ethyl—Cyc—Phe—Phe—A—Alkyl
Propyl—Cyc—Phe—Phe—A—Alkyl
Butyl—Cyc—Phe—Phe—A—Alkyl
Pentyl—Cyc—Phe—Phe—A—Alkyl
Hexyl—Cyc—Phe—Phe—A—Alkyl
Heptyl—Cyc—Phe—Phe—A—Alkyl
Octyl—Cyc—Phe—Phe—A—Alkyl
Nonyl—Cyc—Phe—Phe—A—Alkyl
Decyl—Cyc—Phe—Phe—A—Alkyl
Alkyl—A—Pyr—Methyl
Alkyl—A—Pyr—Ethyl
Alkyl—A—Pyr—Propyl
Alkyl—A—Pyr—Butyl
Alkyl—A—Pyr—Pentyl
Alkyl—A—Pyr—Hexyl
Alkyl—A—Pyr—Heptyl
Alkyl—A—Pyr—Octyl
Alkyl—A—Pyr—Nonyl
Alkyl—A—Pyr—Decyl
Alkyl—A—Pyr—Phe—CN
Alkyl—A—OCO—Phe—CN
Alkyl—A—OCO—Phe—Methyl
Alkyl—A—OCO—Phe—Ethyl
Alkyl—A—OCO—Phe—Propyl
Alkyl—A—OCO—Phe—Butyl
Alkyl—A—OCO—Phe—Pentyl
Alkyl—A—OCO—Phe—Hexyl
Alkyl—A—OCO—Phe—Heptyl
Alkyl—A—OCO—Phe—Octyl
Alkyl—A—OCO—Phe—Nonyl
Alkyl—A—OCO—Phe—Decyl
Alkyl—A—OCO—Phe—Methoxy
Alkyl—A—OCO—Phe—Ethoxy
Alkyl—A—OCO—Phe—Propoxy
Alkyl—A—OCO—Phe—Butoxy
Alkyl—A—OCO—Phe—Pentoxy
Alkyl—A—OCO—Phe—Hexyloxy
Alkyl—A—OCO—Phe—Heptyloxy
Alkyl—A—OCO—Phe—Octyloxy
Alkyl—A—OCO—Phe—Nonyloxy
Alkyl—A—OCO—Phe—Decyloxy
Alkyl—A—OCO—Cyc—CN
Alkyl—A—OCO—Cyc—Methyl
Alkyl—A—OCO—Cyc—Ethyl
Alkyl—A—OCO—Cyc—Propyl
Alkyl—A—OCO—Cyc—Butyl
Alkyl—A—OCO—Cyc—Pentyl
Alkyl—A—OCO—Cyc—Hexyl
Alkyl—A—OCO—Cyc—Heptyl
Alkyl—A—OCO—Cyc—Octyl
Alkyl—A—OCO—Cyc—Nonyl
Alkyl—A—OCO—Cyc—Decyl
Alkyl—A—OCO—Phe—Phe—CN
Alkyl—A—OCO—Phe—Phe—Methyl
Alkyl—A—OCO—Phe—Phe—Ethyl
Alkyl—A—OCO—Phe—Phe—Propyl
Alkyl—A—OCO—Phe—Phe—Butyl
Alkyl—A—OCO—Phe—Phe—Pentyl
Alkyl—A—OCO—Phe—Phe—Hexyl
Alkyl—A—OCO—Phe—Phe—Heptyl
Alkyl—A—OCO—Phe—Phe—Octyl
Alkyl—A—OCO—Phe—Phe—Nonyl
Alkyl—A—OCO—Phe—Phe—Decyl
Alkyl—A—Phe—COO—Cyc—CN
Alkyl—A—Phe—COO—Cyc—Methyl
Alkyl—A—Phe—COO—Cyc—Ethyl
Alkyl—A—Phe—COO—Cyc—Propyl
Alkyl—A—Phe—COO—Cyc—Butyl
Alkyl—A—Phe—COO—Cyc—Pentyl
Alkyl—A—Phe—COO—Cyc—Hexyl
Alkyl—A—Phe—COO—Cyc—Heptyl
Alkyl—A—Phe—COO—Cyc—Octyl
Alkyl—A—Phe—COO—Cyc—Nonyl
Alkyl—A—Phe—COO—Cyc—Decyl
Alkyl—A—Phe—COO—Phe—CN
Alkyl—A—Phe—COO—Phe—Methyl
Alkyl—A—Phe—COO—Phe—Ethyl
Alkyl—A—Phe—COO—Phe—Propyl
Alkyl—A—Phe—COO—Phe—Butyl
Alkyl—A—Phe—COO—Phe—Pentyl
Alkyl—A—Phe—COO—Phe—Hexyl
Alkyl—A—Phe—COO—Phe—Heptyl
Alkyl—A—Phe—COO—Phe—Octyl
Alkyl—A—Phe—COO—Phe—Nonyl
Alkyl—A—Phe—COO—Phe—Decyl
Alkyl—A—Phe—COO—Phe—Methoxy
Alkyl—A—Phe—COO—Phe—Ethoxy
Alkyl—A—Phe—COO—Phe—Propoxy
Alkyl—A—Phe—COO—Phe—Butoxy
Alkyl—A—Phe—COO—Phe—Pentoxy Alkyl—A—Phe—COO—Phe—Hexyloxy
Alkyl—A—Phe—COO—Phe—Heptyloxy
Alkyl—A—Phe—COO—Phe—Octyloxy
Alkyl—A—Phe—COO—Phe—Nonyloxy
Alkyl—A—Phe—COO—Phe—Decyloxy
Alkyl—A—Cyc—COO—Cyc—CN
Alkyl—A—Cyc—COO—Cyc—Methyl
Alkyl—A—Cyc—COO—Cyc—Ethyl
Alkyl—A—Cyc—COO—Cyc—Propyl
Alkyl—A—Cyc—COO—Cyc—Butyl
Alkyl—A—Cyc—COO—Cyc—Pentyl
Alkyl—A—Cyc—COO—Cyc—Hexyl
Alkyl—A—Cyc—COO—Cyc—Heptyl
Alkyl—A—Cyc—COO—Cyc—Octyl
Alkyl—A—Cyc—COO—Cyc—Nonyl
Alkyl—A—Cyc—COO—Cyc—Decyl
Alkyl—A—Cyc—COO—Phe—CN
Alkyl—A—Cyc—COO—Phe—Methyl
Alkyl—A—Cyc—COO—Phe—Ethyl
Alkyl—A—Cyc—COO—Phe—Propyl
Alkyl—A—Cyc—COO—Phe—Butyl
Alkyl—A—Cyc—COO—Phe—Pentyl
Alkyl—A—Cyc—COO—Phe—Hexyl
Alkyl—A—Cyc—COO—Phe—Heptyl
Alkyl—A—Cyc—COO—Phe—Octyl
Alkyl—A—Cyc—COO—Phe—Nonyl
Alkyl—A—Cyc—COO—Phe—Decyl
Alkyl—A—Cyc—COO—Phe—Methoxy
Alkyl—A—Cyc—COO—Phe—Ethoxy
Alkyl—A—Cyc—COO—Phe—Propoxy
Alkyl—A—Cyc—COO—Phe—Butoxy
Alkyl—A—Cyc—COO—Phe—Pentoxy
Alkyl—A—Cyc—COO—Phe—Hexyloxy
Alkyl—A—Cyc—COO—Phe—Heptyloxy
Alkyl—A—Cyc—COO—Phe—Octyloxy
Alkyl—A—Cyc—COO—Phe—Nonyloxy
Alkyl—A—Cyc—COO—Phe—Decyloxy
Alkyl—A—$CH_2CH_2$—Phe—Phe—CN
Alkyl—A—$CH_2CH_2$—Phe—Phe—Methyl
Alkyl—A—$CH_2CH_2$—Phe—Phe—Ethyl
Alkyl—A—$CH_2CH_2$—Phe—Phe—Propyl
Alkyl—A—$CH_2CH_2$—Phe—Phe—Butyl
Alkyl—A—$CH_2CH_2$—Phe—Phe—Pentyl
Alkyl—A—$CH_2CH_2$—Phe—Phe—Hexyl
Alkyl—A—$CH_2CH_2$—Phe—Phe—Heptyl
Alkyl—A—$CH_2CH_2$—Phe—Phe—Octyl
Alkyl—A—$CH_2CH_2$—Phe—Phe—Nonyl
Alkyl—A—$CH_2CH_2$—Phe—Phe—Decyl
Alkyl—A—$CH_2O$—Phe—Pyr—Methyl
Alkyl—A—$CH_2O$—Phe—Pyr—Ethyl
Alkyl—A—$CH_2O$—Phe—Pyr—Propyl
Alkyl—A—$CH_2O$—Phe—Pyr—Butyl
Alkyl—A—$CH_2O$—Phe—Pyr—Pentyl
Alkyl—A—$CH_2O$—Phe—Pyr—Hexyl
Alkyl—A—$CH_2O$—Phe—Pyr—Heptyl
Alkyl—A—$CH_2O$—Phe—Pyr—Octyl
Alkyl—A—$CH_2O$—Phe—Pyr—Nonyl
Alkyl—A—$CH_2O$—Phe—Pyr—Decyl
Alkyl—A—$CH_2CH_2$—Cyc—CN
Alkyl—A—$CH_2CH_2$—Cyc—Methyl
Alkyl—A—$CH_2CH_2$—Cyc—Ethyl
Alkyl—A—$CH_2CH_2$—Cyc—Propyl
Alkyl—A—$CH_2CH_2$—Cyc—Butyl
Alkyl—A—$CH_2CH_2$—Cyc—Pentyl
Alkyl—A—$CH_2CH_2$—Cyc—Hexyl
Alkyl—A—$CH_2CH_2$—Cyc—Heptyl
Alkyl—A—$CH_2CH_2$—Cyc—Octyl
Alkyl—A—$CH_2CH_2$—Cyc—Nonyl, or
Alkyl—A—$CH_2CH_2$—Cyc—Decyl.

11. In a liquid-crystal display element comprising a liquid-crystal phase, the improvement wherein the phase is one of claim 1.

12. In a liquid-crystal display element comprising a liquid-crystal phase, the improvement wherein the phase is one of claim 9.

13. In a liquid-crystal display element comprising a liquid-crystal phase, the improvement wherein the phase is one of claim 7.

14. In a liquid-crystal display element comprising a liquid-crystal phase, the improvement wherein the phase is one of claim 10.

15. In an electrooptical display element comprising a liquid crystalline dielectric, the improvement wherein the dielectric is a liquid-crystal phase of claim 1.

* * * * *